(12) United States Patent
Hendren et al.

(10) Patent No.: US 7,491,217 B1
(45) Date of Patent: Feb. 17, 2009

(54) GRAFT ANCHORING DEVICE

(76) Inventors: Ronald D. Hendren, 750 Mainstreet, Suite 428, Hopkins, MN (US) 55343; Matthew D. Putnam, 5416 Stauder Cir., Edina, MN (US) 55436

( * ) Notice: Subject to any disclaimer, the term of this patent is extended or adjusted under 35 U.S.C. 154(b) by 222 days.

(21) Appl. No.: 11/091,659

(22) Filed: Mar. 28, 2005

Related U.S. Application Data

(63) Continuation-in-part of application No. 10/741,686, filed on Dec. 19, 2003, now abandoned, which is a continuation-in-part of application No. 10/271,923, filed on Oct. 16, 2002, now abandoned.

(60) Provisional application No. 60/330,002, filed on Oct. 16, 2001.

(51) Int. Cl.
*A61B 17/04* (2006.01)

(52) U.S. Cl. ..................... 606/232

(58) Field of Classification Search .......... 606/232, 606/72, 73, 153; 623/13.14
See application file for complete search history.

(56) References Cited

U.S. PATENT DOCUMENTS

| | | |
|---|---|---|
| 4,455,717 A | 6/1984 | Gray |
| 5,236,445 A | 8/1993 | Hayhurste et al. |
| 5,632,748 A | 5/1997 | Beck, Jr. et al. |
| 5,702,397 A * | 12/1997 | Goble et al. ............ 606/72 |
| 5,720,753 A | 2/1998 | Sander et al. |
| 5,725,529 A | 3/1998 | Nicholson et al. |
| 5,733,307 A | 3/1998 | Dinsdale |
| 5,824,087 A | 10/1998 | Aspden et al. |
| 5,931,840 A | 8/1999 | Goble et al. |
| 5,980,558 A | 11/1999 | Wiley |
| 6,086,608 A * | 7/2000 | Ek et al. ............ 606/232 |
| 6,210,412 B1 | 4/2001 | Michelson |
| 6,355,066 B1 | 3/2002 | Kim |
| 6,461,373 B2 | 10/2002 | Wyman et al. |
| 7,147,652 B2 * | 12/2006 | Bonutti et al. ............ 606/232 |
| 2002/0040241 A1 | 4/2002 | Jarvinen |
| 2003/0032982 A1* | 2/2003 | Bonutti et al. ............ 606/232 |
| 2004/0098050 A1* | 5/2004 | Foerster et al. ............ 606/232 |

* cited by examiner

*Primary Examiner*—(Jackie) Tan-Uyen T. Ho
*Assistant Examiner*—Melanie Tyson
(74) *Attorney, Agent, or Firm*—Haugen Law Firm PLLP

(57) ABSTRACT

An apparatus for anchoring a graft segment to a fixed structure in-vivo includes a sleeve member having one or more suture channels extending axially therethrough and an axial opening extending adjacent to the one or more suture channels from a first end of the sleeve member. The apparatus further includes a plug member that is configured for mating engagement within the axial opening of the sleeve member, with such engagement compressing the one or more suture channels to frictionally secure a respective graft suture therein.

15 Claims, 18 Drawing Sheets

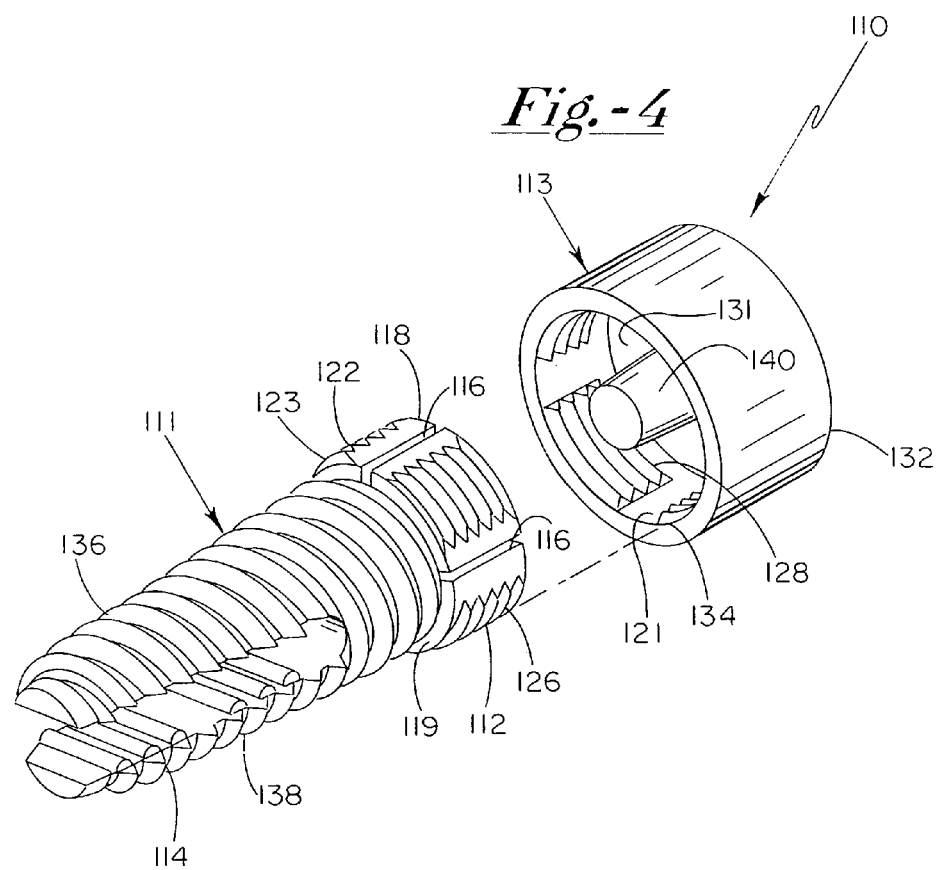

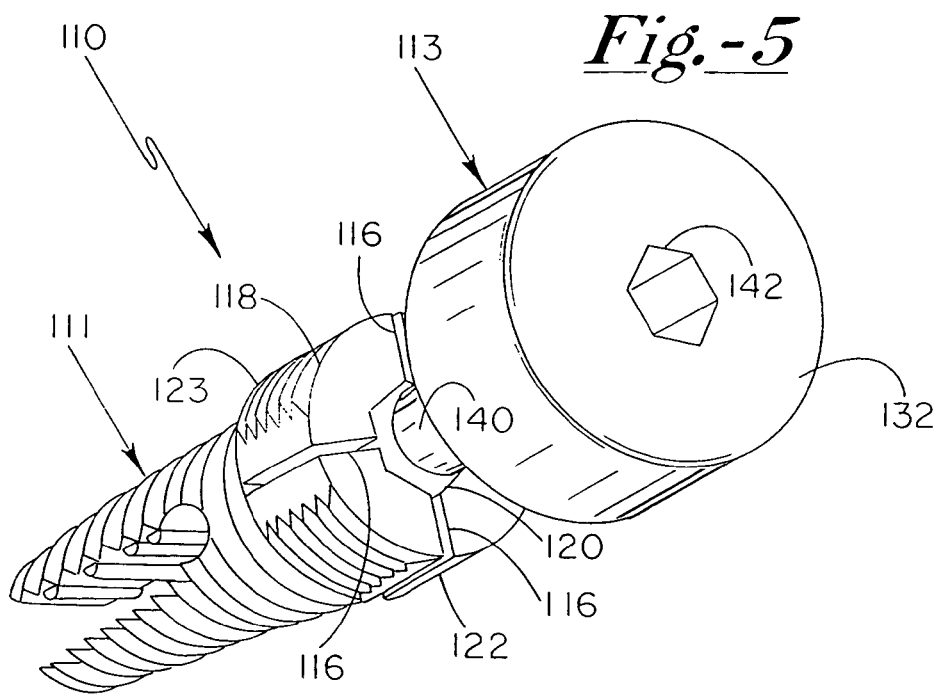
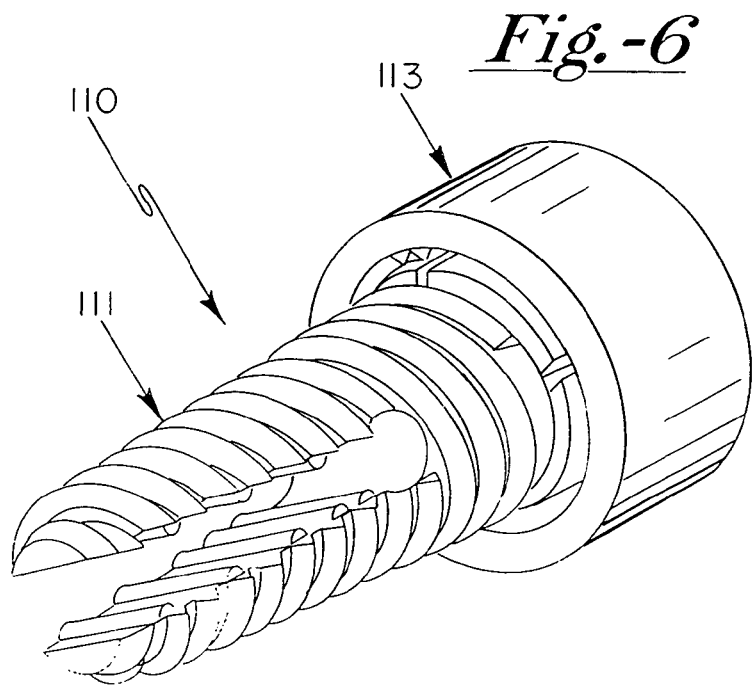

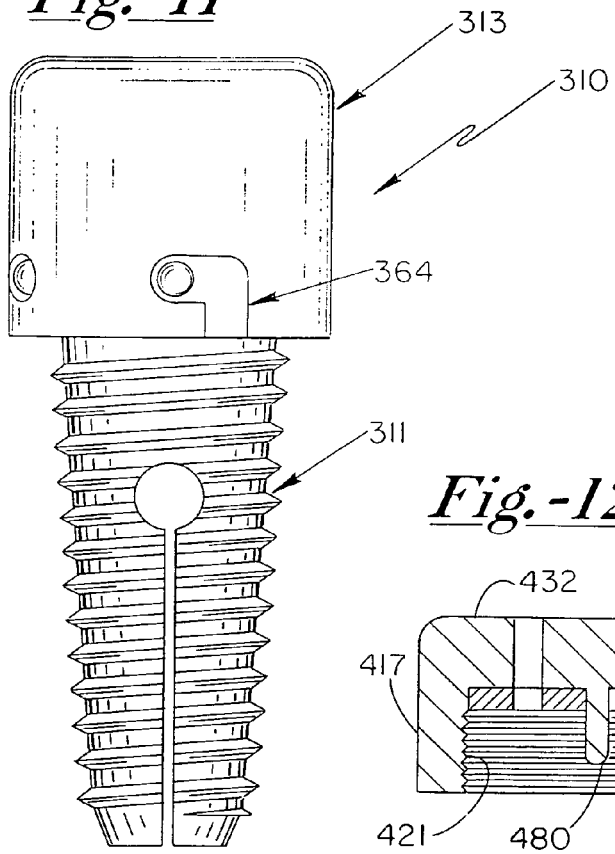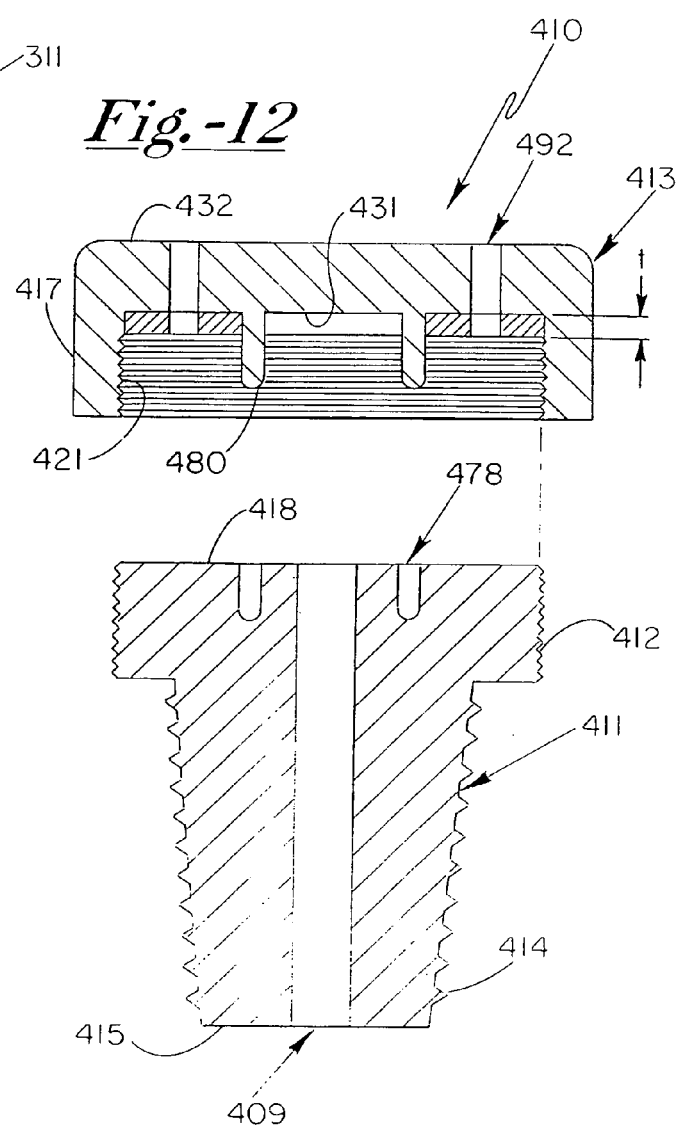

GRAFT ANCHORING DEVICE

CROSS REFERENCE TO RELATED APPLICATIONS

The present application is a continuation-in-part of application Ser. No. 10/741,686, filed Dec. 19, 2003 now abandoned, and entitled "GRAFT ANCHORING DEVICE", which itself is a continuation-in-part of application Ser. No. 10/271,923, filed Oct. 16, 2002 now abandoned, entitled "GRAFT ANCHORING DEVICE", which claims priority from provisional patent application Ser. No. 60/330,002, filed Oct. 16, 2001, and entitled "GRAFT ANCHORING DEVICE", the contents of such applications being incorporated herein in their entirety.

FIELD OF THE INVENTION

The present invention relates to medical grafting implements generally, and more particularly to graft anchoring devices for anchoring grafted material segments to bones or other fixed structures in the body. The present invention also relates to methods for anchoring graft segments to adjacent structures.

BACKGROUND OF THE INVENTION

In vivo grafting procedures have been successfully performed for some time, and have become commonly utilized, particularly in orthopedic procedures. In many of such grafting procedures, a graft segment is harvested from another portion of the patient's body, and utilized to repair or replace damaged ligaments, tendons, or the like. The graft segment is typically attached in some fashion to at least one fixed structure within the body, such as a bone. In particular, the implanted graft segment may take the place of the damaged soft tissue, most commonly by connecting between adjacent bones or between muscle tissue and an adjacent bone. In other procedures, however, such grafted segments are utilized to supplant damaged ligaments, tendons, etc., wherein the implanted graft segment is surgically affixed to a portion of the damaged soft tissue. A vast array of other grafting procedures are commonly performed in the medical field today, and are contemplated as being within the scope of the present invention.

Graft implantation procedures typically utilize an anchoring device to secure the graft segment to one or more fixed structures in vivo. Such anchoring devices act to secure respective graft segments to fixed structures such as bones by being surgically affixed to such structures while operably grasping the graft segment. In preferred procedures, the anchoring device is configured to operably grasp a suture which is surgically connected to the respective graft segment.

A variety of anchoring device configurations have been utilized in procedures requiring the securement of graft material or other soft tissue to adjacent fixed structures. The devices proposed and utilized to date, however, have drawbacks associated with their design or implementation in vivo. In particular, systems and devices in use today for anchoring such graft segments introduce unnecessary complexities and difficulties during a surgical grafting procedure. For example, currently used interference screws which bias a graft segment or suture therefore against a wall of a channel bored into or through a respective fixed structure introduce a risk of damaging or severing the graft and/or suture used to secure the graft material to the anchoring structure. Such damage or severing can result in surgical failure. Other known anchoring devices require specialized operating room equipment, and do not provide adequate error tolerances in their application.

A particular deficiency in current devices is the failure to provide a means for readily altering the suture length or tension in vivo to thereby optimize graft material fit during the surgical process. In such a manner, it is desired to simplify and enhance consistency in grafting procedures.

It is therefore a principle object of the present invention to provide a means for easily and reliably securing graft segments to fixed structures in vivo.

It is a further object of the present invention to provide a graft anchoring means which expedites the graft fixation process so as to reduce overall operating room time necessary.

It is another object of the present invention to provide a graft anchoring means which is specifically configured to securely and automatically grasp a graft suture in vivo without damage thereto.

It is still further object of the present invention to provide a means for optimizing graft tension during the surgical process.

It is a yet further object of the present invention to provide a graft anchoring means which allows for readily altering graft suture length and/or tension in vivo.

SUMMARY OF THE INVENTION

By means of the present invention, the efficiency and reliability of surgical graft implantation procedures is substantially enhanced. Through the utilization of the graft anchoring devices of the present invention, graft segments may more easily be secured to fixed structures, such as adjacent bones, in vivo. Furthermore, the graft anchoring device of the present invention incorporates a configuration which provides a means for adjusting graft segment tension during the implantation procedure. Such adjustability improves the overall rate of success of such grafting procedures.

In a particular embodiment of the present invention, the graft anchoring apparatus includes a suture receiving member having one or more suture receptacles disposed therein, and a fixing member that is specifically configured to matingly engage with the suture receiving member. The mating engagement between the suture receiving member and the fixing member operably compresses the one or more suture receptacles to a degree that is sufficient to secure a respective graft suture therewithin. At least one of the suture receiving member and the fixing member is specifically configured to be frictionally fit in a graft channel in the fixed structure.

The fixing member of the graft anchoring apparatus preferably threadably engages with the suture receiving member. Moreover, the suture receptacles in the suture receiving member are preferably channels extending axially therethrough and in adjacent parallel relationship to an axial opening in the suture receiving member. The fixing member preferably threadably engages within the axial opening of the suture receiving member, and the suture receiving member preferably threadably engages within the graft channel.

In another embodiment of the present invention, the graft anchoring apparatus includes a sleeve member having one or more suture channels extending axially therethrough, and an axial opening extending adjacent to the one or more suture channels from a first end of the sleeve member. The apparatus preferably further includes a plug member that is configured for mating engagement within the axial opening of the sleeve member, with such engagement operably compressing the one or more suture channels to frictionally secure a respective graft suture therein.

A further aspect of the present invention provides a method for anchoring a graft segment to a fixed structure, with the method including providing a graft anchoring apparatus having a sleeve member with one or more suture channels extending axially therethrough and an axial opening extending adjacent to the one or more suture channels from a first end of the sleeve member. The graft anchoring apparatus further includes a plug member being configured for mating engagement with the axial opening of the sleeve member. The method for anchoring the graft segment to the fixed structure further includes forming a graft channel in the fixed structure and affixing a first end of a graft suture to the graft segment, and passing a second end of the graft suture through a respective one of the one or more suture channels in the sleeve member. The plug member is then inserted into the axial opening, thereby securing the suture in the respective suture channel through compression of the suture channels upon respective sutures disposed therein.

Another embodiment of the graft anchoring apparatus of the present invention includes a suture guide member having one or more first suture channels extending axially therethrough, and a first mating structure disposed therewith. The apparatus further includes a suture fixing member having one or more second suture channels extending axially therethrough, and a suture lock mechanism disposed adjacent to respective ones of the second suture channels. The suture fixing member further includes a second mating mechanism that is configured for mating engagement with the first mating structure, with such mating engagement operably causing the first and second suture channels to be in respective axial alignment with one another, such that a first end of a graft suture may operably pass through respective first and second suture channels and be secured to the suture fixing member at the suture lock mechanism.

In another embodiment, the graft anchoring device of the present invention includes a substantially frusto-conical fastener device having a proximal portion and a distal portion. The fastener device is preferably configured such that the diameter at a distal end thereof is relatively smaller then the diameter at a proximal end thereof. The fastener device is threadably inserted and secured in a respective specifically configured graft channel in a fixed structure. The fastener device further includes an open bore axially extending therethrough, with a portion of the open bore at the distal portion of the fastener device being divided into a plurality of distinct suture pathways by a divider, such that individual graft sutures may be operably passed through respective distinct suture pathways so as to prevent the graft sutures from interwinding about one another at the distal portion of the fastener device during the threadable insertion of the fastener device into the graft channel.

A still further embodiment of the graft anchoring apparatus of the present invention includes one or more suture receiving members each having one or more suture receptacles disposed therein, and a displacement member that is specifically configured to matingly engage with the one or more suture receiving members. The mating engagement between the displacement member and the one or more suture receiving members operably compresses the one or more suture receptacles in the one or more suture receiving members to thereby frictionally secure one or more graft sutures within respective ones of the suture receptacles.

BRIEF DESCRIPTION OF THE DRAWINGS

FIG. 4 is a perspective view of a graft anchoring device of the present invention.

FIG. 5 is a perspective view of the graft anchoring device illustrated in FIG. 4.

FIG. 6 is a perspective view of the graft anchoring device illustrated in FIGS. 4 and 5.

FIG. 11 is a side view of the graft anchoring device illustrated in FIGS. 9 and 10.

FIG. 12 is a cross-sectional of a graft anchoring device of the present invention.

DETAILED DESCRIPTION OF THE PREFERRED EMBODIMENTS

The objects and advantages enumerated above together with other objects, features, and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
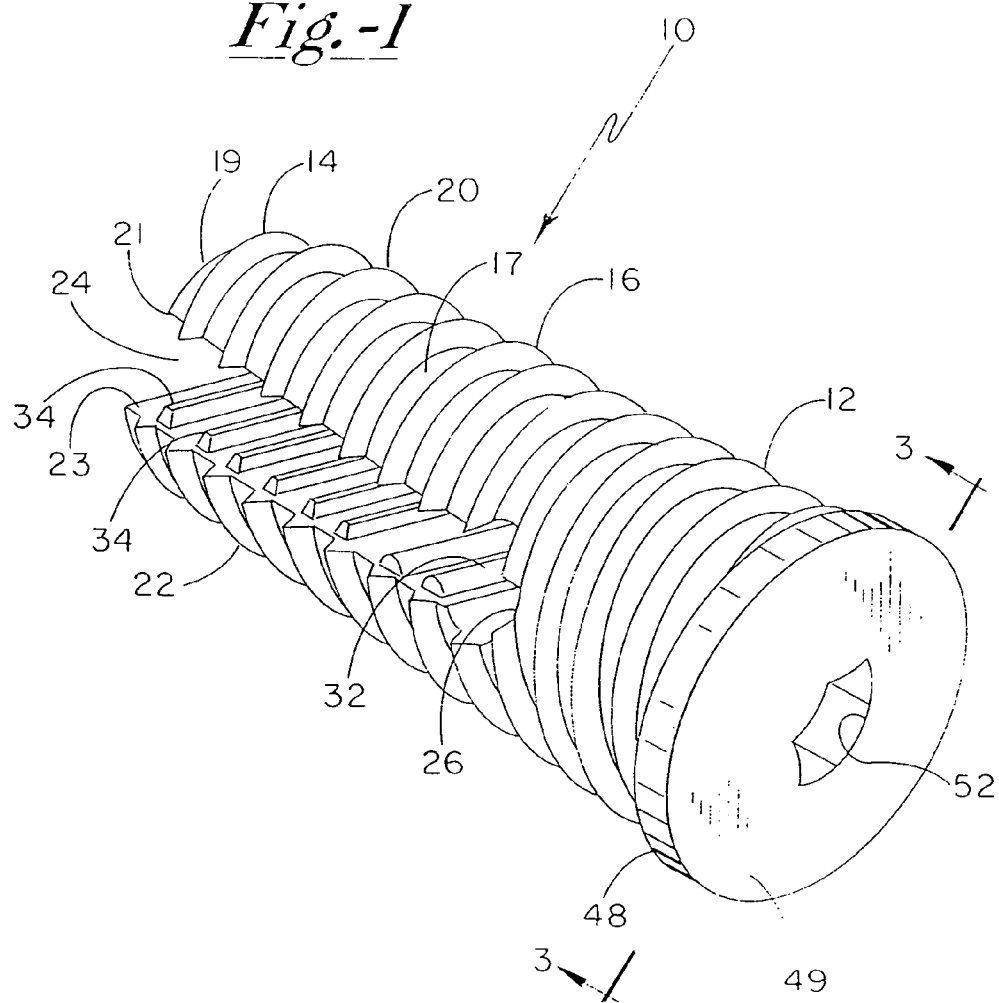
FIG. 1 is a perspective view of a graft anchoring device of the present invention.

With attention now to the drawings, and first to FIG. 1, a graft anchoring device 10 is shown in perspective view. Anchoring device 10 is preferably substantially cylindrical, and most preferably includes a taper such that distal portion 14 has a diameter smaller than that of proximal portion 12 thereof. Such a configuration may be termed frusto-conical. As shown in FIG. 1, anchoring device 10 preferably includes threads 16 on an outer surface 17 thereof, which threads 16 are preferably configured in a 60 degree v thread orientation, though a variety of other thread configurations may be implemented as desired. Anchoring device 10 may alternatively be configured with securement means other than, or in addition to, threads 16. For example, anchoring device 10 may be press fit into place in vivo without threadable actuation.

As shown in FIG. 1, distal portion 14 of anchoring device 10 is preferably initially formed in a bifurcated configuration, whereby a first distal arm 20 is separated from a second distal arm 22 by a substantially wedge-shaped gap 24 disposed therebetween. Gap 24 is preferably configured such that, in an unstressed condition, separation between first and second distal arms 20, 22 increases toward distal end 19 of anchoring device 10. Such a configuration for gap 24, however, may be modified to accomplish specific attributes desired for particular applications.

In preferred embodiments, a stress relief zone 32 is provided adjacent to an apex 26 of gap 24. In use, gap 24 of anchoring device 10 is compressed while being inserted into a bored graft channel in a respective fixed structure as a result of the frusto-conical configuration of anchoring device 10. As a result of such compressive displacement of first and second distal arms 20, 22, stress forces are developed in anchoring device 10; and are particularly focused in proximal portion 12 of anchoring device 10. To accommodate such stress forces without damage to anchoring device 10, stress relief zone 32 is provided to absorb such forces, and to minimize detrimental effects on anchoring device 10. Stress relief zone 32 is preferably a hollowed out portion of anchoring device 10, whereby bending moments generating such stress forces may be dissipated in a non-damaging manner.

Figure 2:
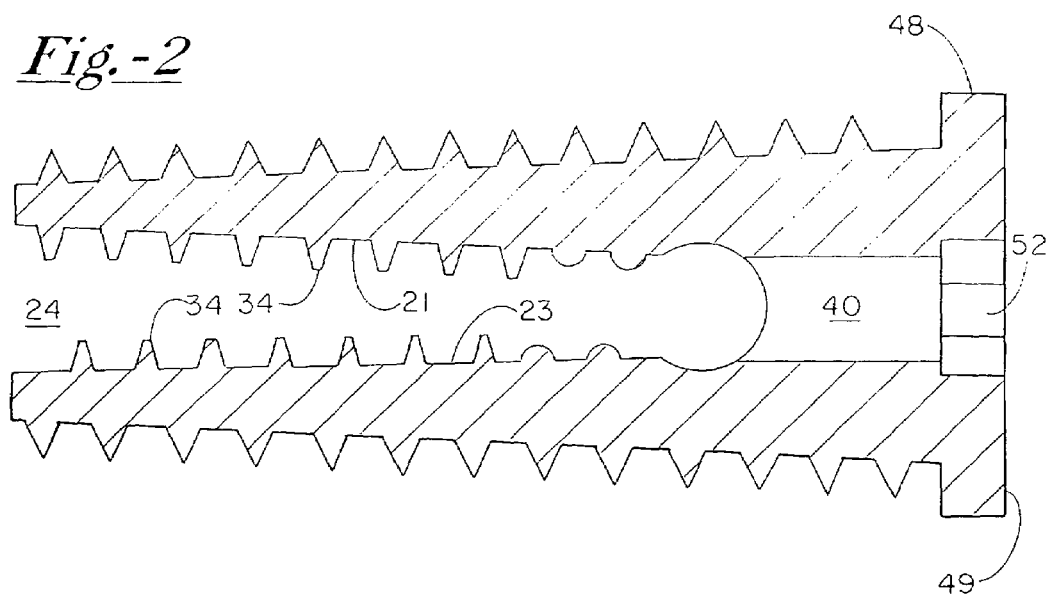
FIG. 2 is a cross-sectional view of a graft anchoring device of the present invention.

FIG. 2 illustrates a cross-sectional view of anchoring device 10. As can be seen more clearly in FIG. 2, respective inner surfaces 21, 23 of first and second distal arms 20, 22 preferably include one or more clasping protrusions 34 extending therefrom. In preferred embodiments, a plurality of clasping protrusions 34 are arrayed on respective surfaces 21, 23 in substantially linear configurations. As shown in FIG. 2, a plurality of groups of such clasping protrusions 34 are disposed in substantially opposed relationship on respective inner surfaces 21, 23. Clasping protrusions 34 are preferably configured to graft suture material (not shown) passing through gap 24 and a cannulated portion 40 of anchoring device 10. Cannulated portion 40 substantially comprises an open bore axially extending at least partially through proximal portion 12 of anchoring device 10. Preferably, however, cannulated portion 40 extends through proximal portion 12.

As further illustrated in FIG. 2, one or more clasping protrusions 34 proximal to cannulated portion 40 preferably include a substantially semi-circular profile or cross-section. Such a rounded profile minimizes cuts or abrasions to the respective suture material threaded through device 10 when first and second distal arms 20, 22 compress toward one another during insertion in vivo. The portion of device 10 adjacent to apex 26 of gap 24 typically encounters the highest levels of suture stress during the implantation procedure. As a result, it is beneficial to reduce or eliminate sharp points which are likely to cause suture abrasion within device 10 during the graft implantation procedure.

In operation, distal arms 20, 22 are compressed toward one another thereby bringing respective grasping protrusions 34 into close proximity with one another. The close proximity of such grasping protrusions 34 acts to grasp or grip the aforementioned suture between respective distal arms 20, 22 of anchoring device 10.

In some embodiments, grasping protrusions 34 are unidirectionally oriented to further assist in preventing the suture material from distally moving with respect to anchoring device 10 when respective distal arms 20, 22 are displaced toward one another. In such a manner, an enhanced "locking means" is provided for holding the suture material in place within anchoring device 10.

In a particular embodiment of the present invention, respective grasping protrusions 34 are disposed in offset opposing relationship with one another. Such an offset orientation diminishes likelihood of damage to the suture material during compression of respective distal portions 20, 22 toward one another. In addition, such offset orientation advantageously acts to further lock the suture material within anchoring device 10, as the offset grasping protrusions 34 preferably at least partially overlap one another in a fully compressed configuration.

Figure 3:
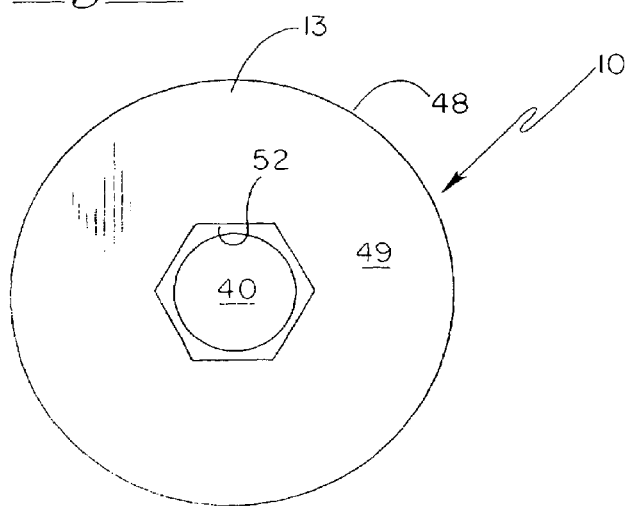
FIG. 3 is an end view of the proximal portion of a graft anchoring device of the present invention.

FIG. 3 is an end view of proximal portion 12 of anchoring device 10. As shown in FIGS. 1 and 3, proximal portion 12 of anchoring device 10 preferably includes a flange means 48 that is disposed at a proximal end 13 of anchoring device 10. Flange means 48 preferably acts to prevent over-insertion of anchoring device 10 into the respective fixed structure by forming a relatively larger circumferential area than is provided by the respective bored channel in the fixed structure. As seen in FIG. 3, the hollow cannulated portion 40 preferably extends through an entire length of anchoring device 10. In other embodiments, however, an open channel configured to receive the suture material may be disposed in only portions of anchoring device 10 as desired. Preferably, however, the suture material may be completely passed through anchoring device 10 such that a user may grasp the suture material at a location displaced from proximal portion 12 of anchoring device 10. In such a manner, the user may adjust the tension of the graft segment while simultaneously securing anchoring device 10 to the respective fixed structure. Therefore, the overall "fit" of the graft segment may be adjusted during the grafting procedure to obtain the best possible surgical results.

The illustration of FIG. 3 further depicts a tool receiving recess 52 (actuation means) disposed in outer surface 49 of flange means 48. Tool receiving recess 52 is preferably configured to receive standard-sized rotation tools such as screwdrivers, ratchet devices, and the like. In a particular embodiment, tool receiving recess 52 is preferably configured to receive hexagonal-shaped tools. Other configurations, however, may be implemented for use with variously-shaped tools. Most preferably, such tools are cannulated to provide an axial bore therethrough so that the suture may be threaded through the bore and grasped by the user.

Anchoring device 10 may be fabricated from a variety of materials, though materials compatible in use in-vivo are most preferred. In particular, various bio-absorbable materials are preferred for advantageous in-vivo acceptance, as well as reduced interference with other medical procedures, such as MRI studies.

A particular application envisioned for the anchoring device of the present invention is in attaching a proximal end of surgical grafts, particularly those used in anterior cruciate ligament (ACL) reconstruction procedures. In current procedures, arthroscopic techniques are utilized for ligament and other graft-requiring repairs. Typically, the surgical area is entered via one or more ports formed in the exterior of the subject body. In an ACL reconstruction operation, tunnels are drilled in adjacent portions of the patient's tibia and femur, between which the graft material is to be placed. A distal end of an elongated suture material is preferably attached to a graft segment prior to entering the surgical area. A proximal end or portion of the suture material is preferably threaded through an eyelet of a guide wire, which guide wire is then directed through the respective tibial and femoral tunnels, thereby positioning the graft segment in place between the femur and the tibia. To secure or anchor the graft segment to the femur, which acts as an anchoring or fixed structure, the proximal end of the suture material is preferably threaded through the cannulated portion 40 of anchoring device 10, such that the proximal portion of the suture material extends from distal portion 14 through proximal portion 12, and beyond flange means 48 of anchoring device 10. The user is then able to grasp the proximal end of the suture material while rotatably inserting anchoring device 10 into a respective proximal end of the femoral tunnel. Continued rotational insertion therein causes respective distal arms 20, 22 to displace toward one another, in turn causing grasping protrusions 34 to engage and correspondingly "lock" the suture material in place. By tightly grasping the suture material, the inserted graft segment is correspondingly held securely in place. In addition, rotatable installation of the device into the tunnel while grasping the suture material results in a "braiding" effect upon the suture material, which enhances the tautness of the final graft anchoring. The above-described procedure significantly minimizes time, complexity, and difficulty associated with anchoring techniques presently utilized.

An additional embodiment of the present invention is illustrated in the perspective view of FIG. 4, wherein a graft anchoring device 110 includes an anchoring element 111 and a cap element 113. Anchoring element 111 is substantially akin to anchoring device 10, with anchoring element 111 being substantially frusto-conical in configuration and having a proximal portion 112 and a distal portion 114, with the diameter of anchoring element 111 being larger at proximal portion 112 than at distal portion 114.

As illustrated in FIGS. 4 and 5, proximal portion 112 of anchoring element 111 includes one or more locking notches 116 disposed therein. Locking notches 116 are preferably configured as grooves or recesses disposed in proximal end 118 of proximal portion 112, such that locking notches 116 are orthogonally positioned with respect to proximal bore end 120. Locking notches 116 are preferably substantially v-shaped in cross-section, such that suture material secured to a respective graft segment being anchored may be operably passed through proximal bore end 120 and placed into a respective one of the locking notches 116 for operably retention therein. The v-shaped cross-section of such locking notches 116, along with their relative orthogonal orientation to proximal bore end 120 operate in combination to frictionally retain the suture material in place, and preferably under tension, within a respective locking notch 116. In other words, the tension forces developed in the suture for anchoring the graft segment to a fixed structure act in an axial direction with respect to anchoring element 111. Therefore, frictionally grasping the suture material in a radial direction, as in locking notches 116, assists in resisting such tension forces thereby securely retaining the suture material in a fixed position.

In preferred embodiments of the present invention, locking notches 116 are further formed in side surface 122 of proximal portion 112. Such a configuration for locking notches 116 provides a still greater degree of suture material securement therewithin by adding an additional orthogonal locking orientation.

As shown in FIGS. 4-6, cap element 113 is preferably configured so as to be matingly engageable with proximal portion 112 of anchoring element 111. Preferably, cap element 113 matingly engages proximal portion 112 in a superimposed orientation therewith, such that an inner side surface 121 of cap element 113 is operably disposed adjacent to side surface 122 of proximal portion 112 when cap element 113 is matingly engaged with anchoring element 111. In preferred embodiments of the present invention, cap element 113 may be threadably engaged with proximal portion 112 via threads 126, 128 respectively disposed on engaging surfaces of proximal portion 112 and cap element 113, and particularly on side surface 122 of proximal portion 112, and inner side surface 121 of cap element 113.

Operably engaging cap element 113 to proximal portion 112 of anchoring element 111 preferably acts to further secure a respective graft suture to proximal portion 112 by frictionally interposing the graft suture between proximal portion 112 and inner side surface 121 of cap element 113. Therefore, in embodiments incorporating locking notches 116 in side surface 122 of proximal portion 112, graft suture material is preferably at least partially retained therein. Upon mating engagement of cap element 113 to proximal portion 112, compression forces are developed upon such suture material as a result of being tightly interposed between cap element 113 and proximal portion 112. Such compression forces result in substantial frictional resistance being formed at the surface interfaces between the graft suture material and one or both of proximal portion 112 and cap element 113.

Cap element 113 preferably includes an axial protrusion 140 extending from an inner surface 131 of first closed end 132. Axial protrusion 140 is preferably specifically configured to extend at least partially into proximal bore end 120 when cap element 113 is operably engaged with anchoring element 111. Axial protrusion 140 is preferably substantially hemispherical in configuration, though a wide variety of other configurations for axial protrusion 140 are contemplated by the present invention. By at least partially extending into proximal bore end 120 during the operable engagement of cap element 113 to anchoring element 111, the respective graft suture extending through proximal bore end 120 is operably pinched between axial protrusion 140 and proximal portion 112 of anchoring element 111. An enhanced degree of frictional retention of the graft suture element at proximal portion 112 is thereby achieved through the pressure generated by axial protrusion 140 extending at least partially into proximal bore end 120.

As illustrated in FIG. 5, cap element 113 preferably includes an actuation means 142 disposed in first closed end 132 thereof. Actuation means 142 is illustrated as a recess that is specifically configured so as to receive a standard surgical tool, such as a hex-head screw driver. Other configurations for actuation means 142 are contemplated by the present invention, including both as recesses or as protrusions or combinations thereof. Actuation means 142 is preferably utilized to operably engage cap element 113 with proximal portion 112 of anchoring element 111. In preferred embodiments, such engagement is through threadable engagement between the respective components of graft anchoring device 110. Thus, actuation means 142 may be utilized to threadably engage cap element 113 onto anchoring element 111. In addition, when cap element 113 is tightly engaged upon proximal portion 112 of anchoring element 111, continued rotational actuation of cap element 113 via actuation means 142 results in the rotation of the entire graft anchoring device 110. In such a manner, continued rotational actuation of cap element 113 via actuation means 142 provides for a means to threadably insert graft anchoring device 110 into a respective graft channel in a fixed structure in vivo.

Distal portion 114 of anchoring element 111 is preferably divided into a first leg portion 136 and a second leg portion 138. The embodiment illustrated in FIGS. 4-6 depicts each of first and second leg portions 136, 138 having respective facing flat inner surfaces having arrays of clasping protrusions disposed thereon. In other embodiments, however, first and second leg portions 136, 138 may be free from such clasping protrusions and/or may be substantially concave in configuration so as to obtain a substantially cannulated configuration for distal portion 114 of anchoring element 111.

Figure 7:
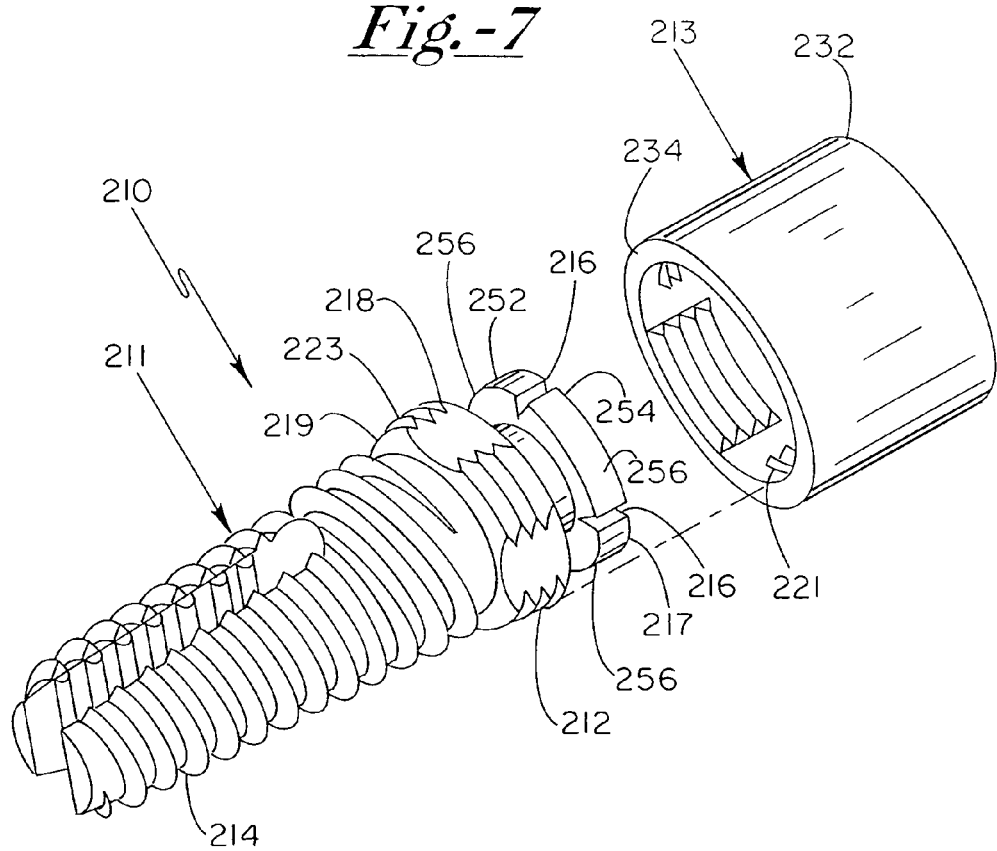
FIG. 7 is a perspective view of a graft anchoring device of the present invention.
Figure 8:
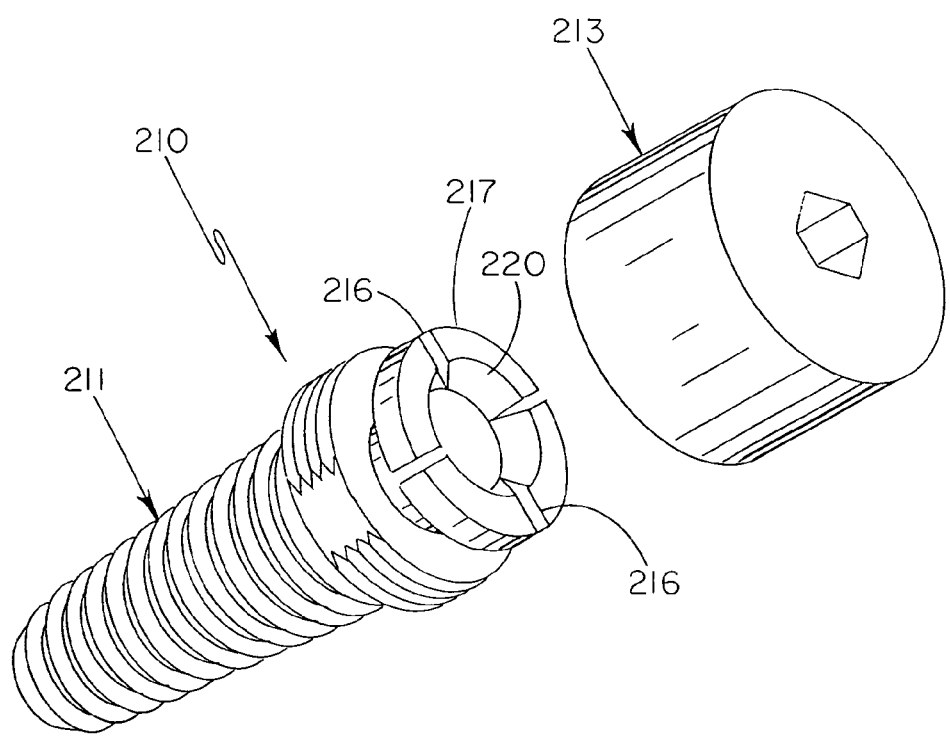
FIG. 8 is a perspective view of the graft anchoring device illustrated in FIG. 7.

An additional embodiment of the present invention is illustrated at FIGS. 7 and 8, with anchoring element 211 including a proximal portion 212 and a distal portion 214, and further including a locking ring 252 integrally formed therewith and disposed adjacent to proximal portion 212. As illustrated in FIG. 7, locking ring 252 is preferably coaxially positioned with respect to proximal portion 212, and includes one or more locking notches 216 disposed in at least a first end surface 217 of locking ring 252. In preferred embodiments of the present invention, locking notches 216 extend orthogonally with respect to proximal bore end 220, and further extend into and along a side surface 254 of locking ring 252. As so disposed in locking ring 252, locking notches 216 form a plurality of distinct locking ring portions 256 that are partially separated by the one or more locking notches 216.

In some embodiments of the present invention, proximal portion 212 of anchoring element anchoring element 211 is tapered such that a diameter at proximal end 218 is relatively smaller than a diameter at base 219 of mating portion 223. In such a manner, operably engagement of cap element 213 with proximal portion 212 of anchoring element 211 compresses locking ring portions 256 toward one another, thereby tightening the clasping arrangement of respective adjacent locking ring portions 256 about the respective graft suture. Alternatively, inner side surface 221 of cap element 213 may be tapered such that a diameter adjacent first closed end 232 is relatively smaller than a diameter of inner side surface 221 at second open end 234. Such an arrangement operably achieves the same results as that described above.

Figure 9:
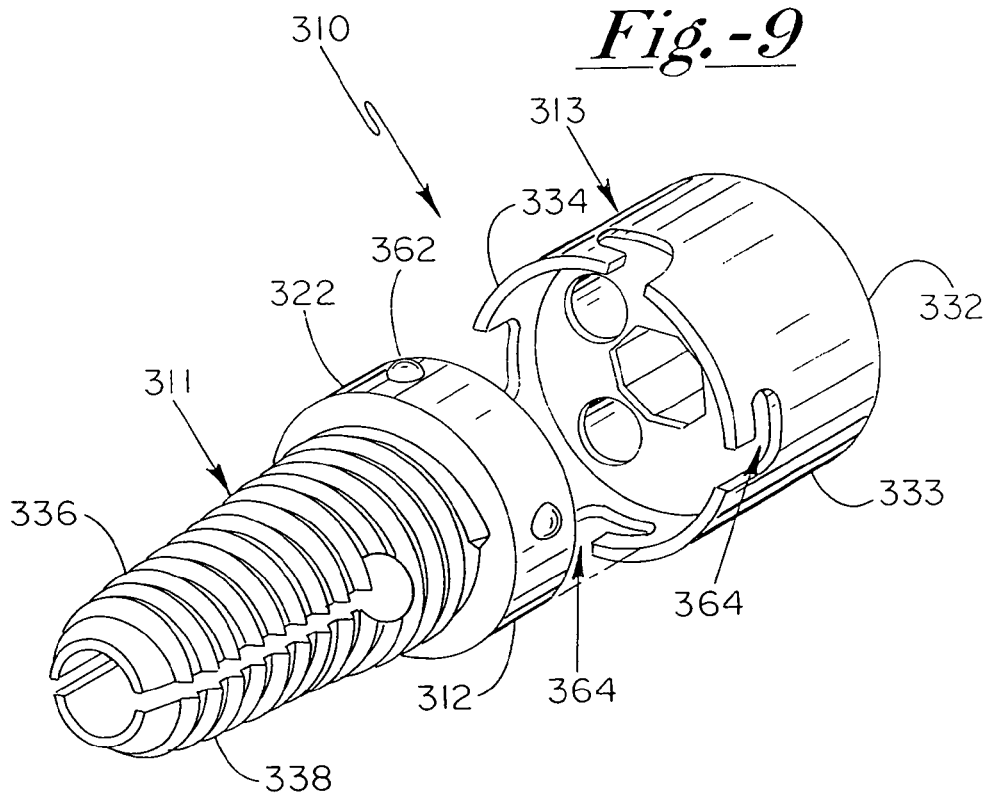
FIG. 9 is a perspective view of a graft anchoring device of the present invention.
Figure 10:
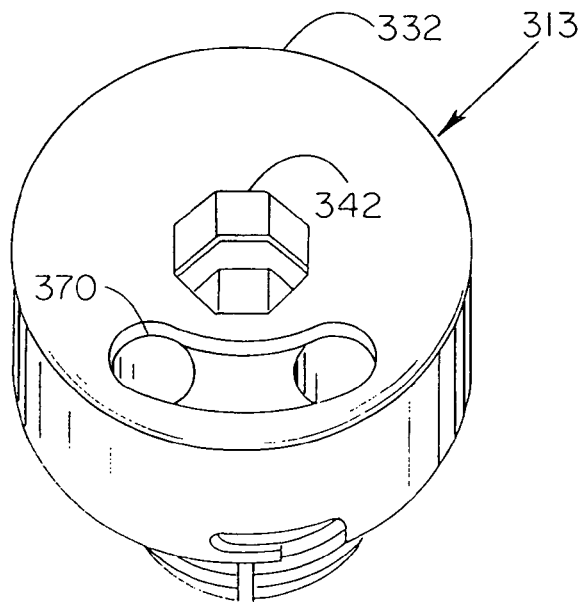
FIG. 10 is a top end view of the graft anchoring device illustrated in FIG. 9.

A further embodiment of the present invention, is illustrated in FIGS. 9-11, and provides for an alternative mating engagement means between cap element 313 and anchoring element 311 of graft anchoring device 310. Proximal portion 312 of anchoring element 311 preferably includes one or more protuberances 362 disposed on a side surface 322 thereof. To operably engage cap element 313 with anchoring element 311, such protuberances 362 are preferably operably received in respective one or more cut-out slots 364 in side wall 333 of cap element 313. A shown in FIG. 9, such cut-out slots 364 extend from second open end 334 of side wall 333 toward first closed end 332 thereof. In addition, such cut-out slots 364 preferably have a transverse portion extending substantially parallel to second open end of cap element 313, such that operable reception of respective protuberances 362 in cut-out slots 364 acts to operably and securely engage cap element 313 to anchoring element 311. In operation, cap element 313 is positioned in a partially superimposed orientation about proximal portion 312 of anchoring element 311, with protuberances 362 being received in respective cut-out slots 364. To securely engage cap element 313 to anchoring element 311, cap element 313 is subsequently rotated (in a counter-clockwise direction in the embodiment illustrated in FIGS. 9-11) so as to cause such protuberances 362 to be operably received in the respective transverse portions of cut-out slots 364. In such a manner, axial separation between cap element 313 and anchoring element 311 is therefore prevented. FIG. 11 illustrates cap element 313 in an operably engaged orientation with anchoring element 311.

As is best illustrated in FIGS. 9 and 10, cap element 313 preferably includes an actuation means 342 that may be configured as a bore extending axially through cap element 313, or may be a recess, protrusion, or combination thereof. The present invention contemplates a configuration for actuation means 342 that corresponds to standard surgical tools for simple connection between such tools and cap element 313. In addition, cap element 313 may further include one or more graft suture bores 370 extending therethrough from first closed end 332. Such graft suture bores 370 allow a surgeon to pull upon a free end of the graft suture material as it extends through graft anchoring device 310 while graft anchoring device 310 is being operably inserted into a corresponding graft channel in a fixed structure in vivo. In doing so, the surgeon may keep the graft suture material taut during the anchoring process to thereby achieve a preferred graft segment construction.

FIG. 9 further illustrates an example of the cannulated configuration for anchoring element 311, wherein the respective inner surfaces of first and second leg portions 336, 338 are substantially concave. The present invention, however, contemplates various inner side surface configurational characteristics for anchoring element 311. For example, anchoring element 311, as well as all anchoring elements described herein may form a single cylindrical channel formed within a solid body distal portion 314 thereof. As such, distal portion 314 may not be divided into first and second leg portions 336, 338, but may rather be formed as a singular tapered body.

Figure 13:
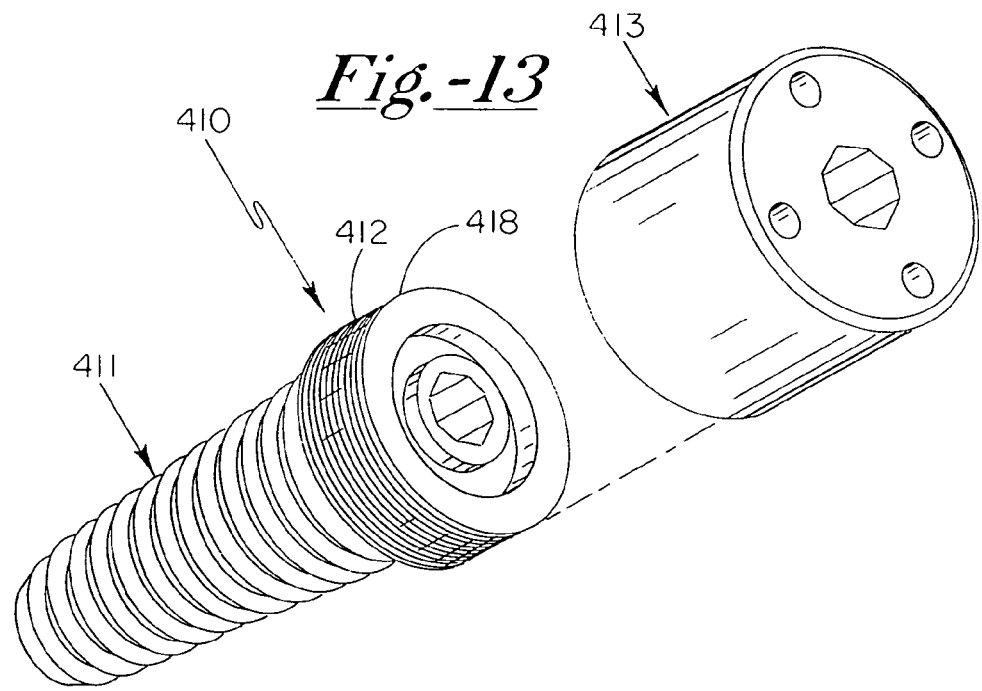
FIG. 13 is a perspective view of the graft anchoring device illustrated in FIG. 12.
Figure 14:
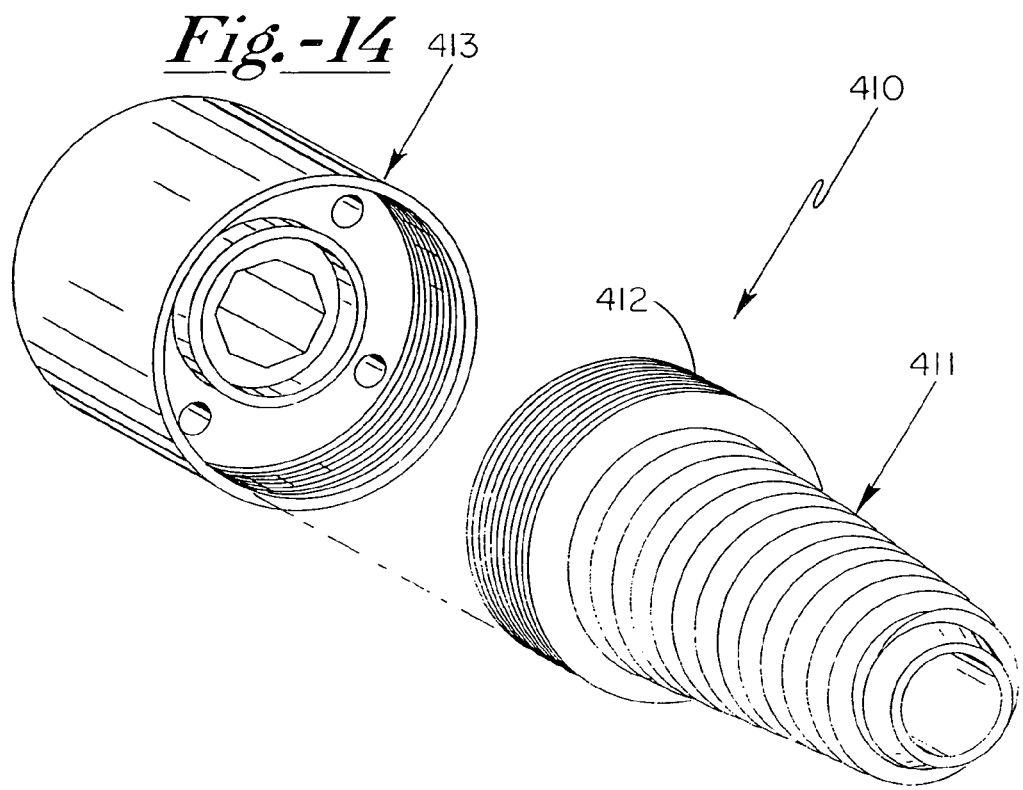
FIG. 14 is a perspective view of the graft anchoring device illustrated in FIGS. 12 and 13.
Figure 15:
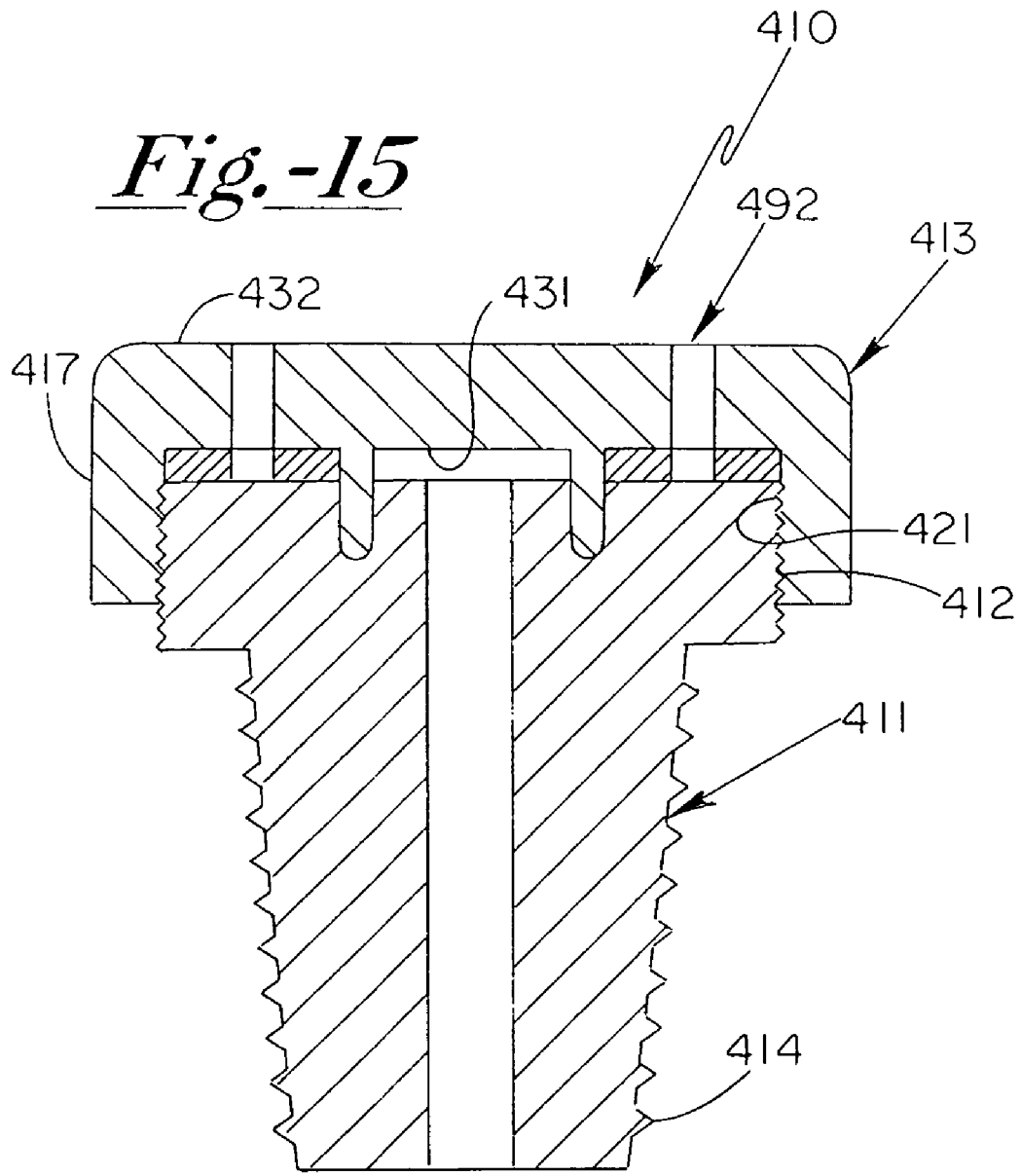
FIG. 15 is a side view of the graft anchoring device illustrated in FIGS. 12-14.

An additional embodiment of the present invention is illustrated in FIGS. 12-15, with attention first being drawn to the cross-sectional view of FIG. 12. Graft anchoring device 410 includes an anchoring element 411 and a cap element 413, with anchoring element 411 having a proximal portion 412 and a distal portion 414. Anchoring element 411 further includes an open channel 409 extending axially therethrough from a proximal end 418 to a distal end 415 thereof. Proximal end 418 of anchoring element 411 preferably includes an annular groove 478 disposed therein, which annular groove 478 serves as a receiving means for operably receiving a correspondingly configured annular protrusion 480 extending from inner surface 431 of first end 432 of cap element 413. As such, annular protrusion 480 acts as a mating means for matingly engaging with the receiving means in proximal portion 412 of anchoring element 411 that is formed by annular groove 478. Such mating engagement therebetween is illustrated in FIG. 15 with cap element 413 being operably engaged with proximal portion 412 of anchoring element 411.

In the embodiment illustrated in FIGS. 12-15, annular groove 478 is coaxially disposed about open channel 409, which defines a central axis of anchoring element 411. As such, threadable engagement of cap element 413 to proximal portion 412 of anchoring element 411 allows for smooth insertion of annular protrusion 480 into annular groove 478. Other respective configurations, however, are contemplated by the present invention for operably engagement between a receiving portion and a corresponding protrusion portion on one or both of cap element 413 and/or anchoring element 411.

As is further illustrated in FIG. 12, cap element 413 further includes a stop means 482, which may be in the form of an annular ring coaxially surrounding annular protrusion 480. Stop means 482 may be integrally formed with inner surface 431 of first end 432, or may alternatively be a distinct element disposed upon inner surface 431 and between an inner side surface 421 of side wall 417 and annular protrusion 480. Preferably, stop means 482 is specifically configured so as to arrest the depth of progressive engagement of cap element 413 upon and onto proximal portion 412 of anchoring element 411 by coming into contact with proximal end 418 of proximal portion 412 during such progressive engagement. More preferably, stop means 482 has a predetermined and calibrated thickness "t" which acts to operably arrest the progressive engagement of cap element 413 so as to effect a specific degree of engagement between annular protrusion 480 and annular groove 478.

In operation, graft suture material is fed through open channel 409 and preferably through a respective cap aperture 492 such that the physician may operably grasp an end of such graft suture during the graft anchoring procedure. With the graft suture being in such an operable orientation, engagement of cap element 413 to anchoring element 411 causes the graft suture to be operably trapped between the progressively engaging annular protrusion 480 within annular groove 478. Such entrapment of the graft suture material effects a frictional retention and securement of the graft suture to graft anchoring device 410.

It is contemplated by the present invention that different anchoring procedures require various graft suture tensions, which graft suture tensions may be automatically achieved through a predetermined extent of engagement between cap element 413 and anchoring element 411. This effect may be accomplished through the predetermined and calibrated thickness "t" of stop means 482, whereby a relatively thinner stop means 482 provides a greater degree of progressive engagement between cap element 413 and anchoring element 411, and correspondingly results in a relatively higher tension developed in the securement of the graft suture material to graft anchoring device 410. Conversely, a relatively thicker stop means 482 results in a correspondingly lesser degree of engagement between cap element 413 and anchoring element 111, thereby decreasing the degree into which annular protrusion 480 extends into annular groove 478, and consequently results in a relatively lower tension developed in the graft suture material as anchored to graft anchoring device 410. Accordingly, it is an important aspect of the present invention to provide a predetermined and calibrated thickness of stop means 482 so as to automatically create a predetermined tension in a graft suture being secured within annular groove 478 by annular protrusion 480.

Cap element 413 preferably includes one or more cap apertures 492 that provide an access means for the physician to grasp an end of a graft suture and to hold such suture in a taut relationship during the mating engagement of cap element 413 to anchoring element 411 in the graft anchoring process.

A further embodiment of the present invention is illustrated in FIGS. 16-19, wherein graft anchoring apparatus 510 includes a sleeve member 512 having suture channels 514 extending axially therethrough. In the embodiments illustrated in FIGS. 16-19, suture channels 514 form semi-annular bores extending axially through and along sidewall 516 of sleeve member 512. Suture channels 514 are interrupted in an annular path about a central axis 518 of sleeve member 512 by support struts 520 which connect outer wall 522 to inner wall 524 of sleeve member 512. A wide variety of other configurations for suture channels 514, however, are contemplated by the present invention, and are preferably limited only to the extent that such suture channels 514 be sized and configured to operably receive a graft suture therein.

Sleeve member 512 preferably further includes an axial opening or aperture 526 that extends adjacent to suture channels 514 at least from first end 513 of sleeve member 512. As shown in FIGS. 16-19, axial opening 526 preferably extends radially about central axis 518, such that suture channels 514 are perimetorally disposed thereabout. In other embodiments, however, axial opening 526 may instead be disposed at other locations within sleeve member 512, with the critical aspect of the location of axial opening 526 being the relative proximity to suture channels 514 for the purpose described hereinbelow. In preferred embodiments, axial opening 526 may extend substantially through an entire length "L" of sleeve member 512, and is preferably inwardly tapered from first end 513, such that a diameter of axial opening 526 at first end 513 is greater than the diameter of axial opening 526 at or adjacent to second end 515 of sleeve member 512.

Figure 16:
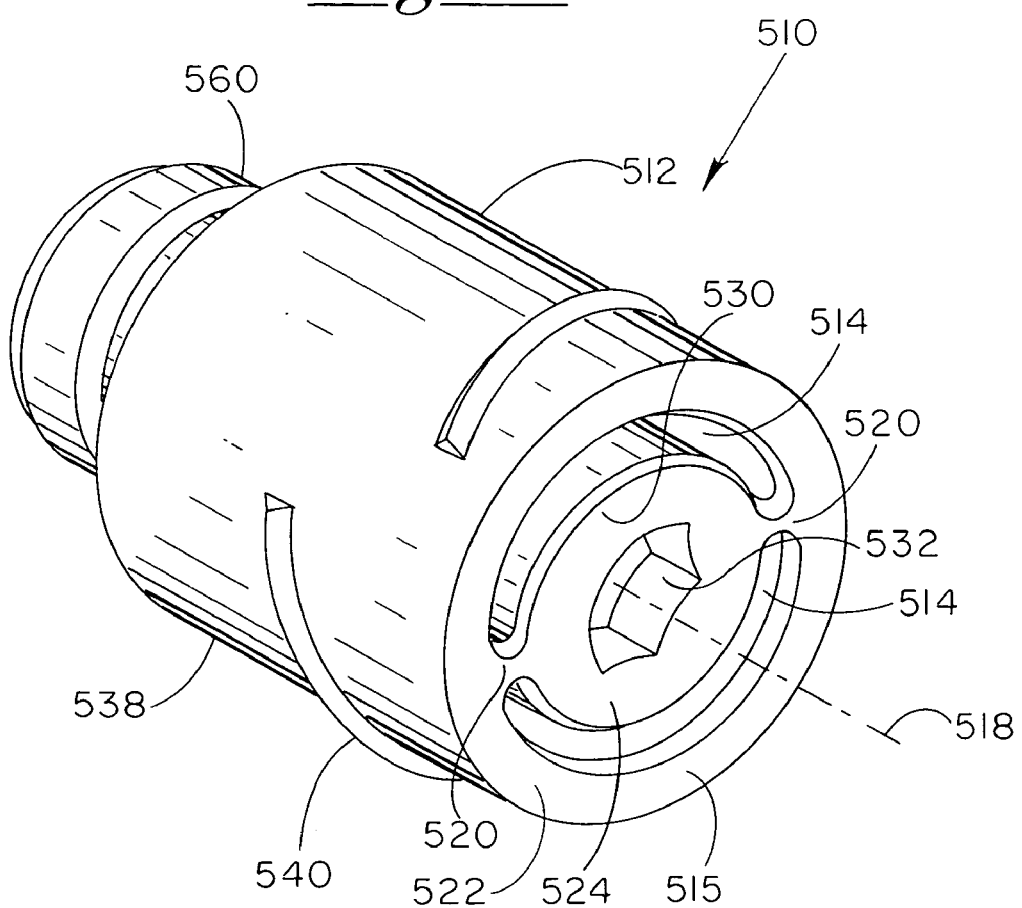
FIG. 16 is a perspective view of a graft anchoring apparatus of the present invention.
Figure 17:
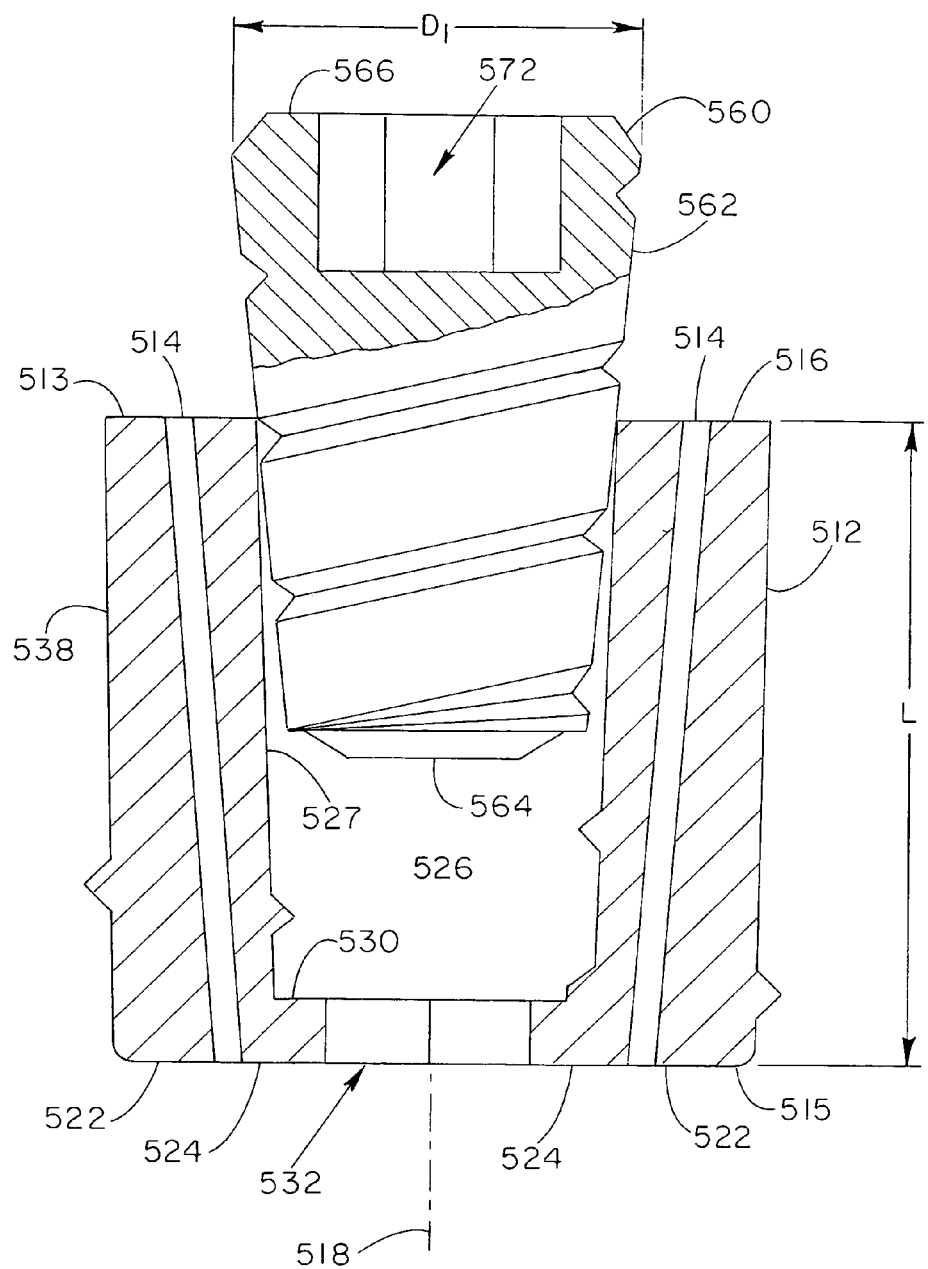
FIG. 17 is a side cross-sectional view of the graft anchoring apparatus illustrated in FIG. 16.

As best seen in FIGS. 16 and 17, sleeve member 512 preferably includes a stop flange 530 at second end 515, with stop flange 530 extending radially inwardly into axial opening 526. Stop flange 530 preferably acts as an abutment to arrest over-insertion of plug member 560 into axial opening 526 of sleeve member 512. In addition, stop flange 530 preferably defines an actuation aperture 532 that is specifically configured to receive an actuation tool therein. Actuation aperture 532 may therefore be in the form of a hexagonal opening, such that a hex wrench or a screwdriver with a hexagonal head may be used to engage within actuation aperture 532 to rotate sleeve member 512 about axis 518.

Figure 18:
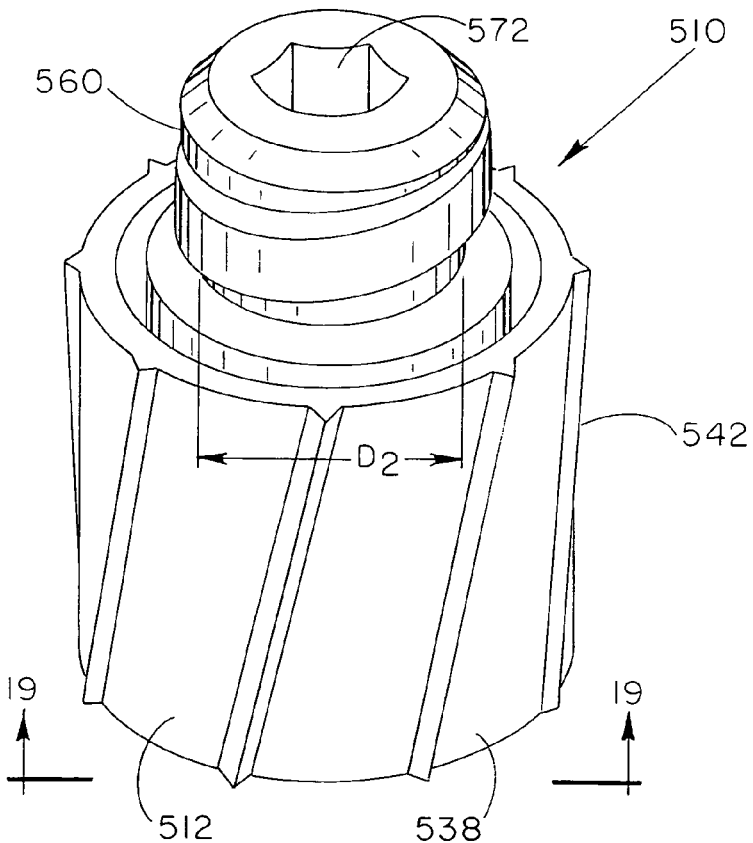
FIG. 18 is a top perspective view of a graft anchoring apparatus of the present invention.
Figure 19:
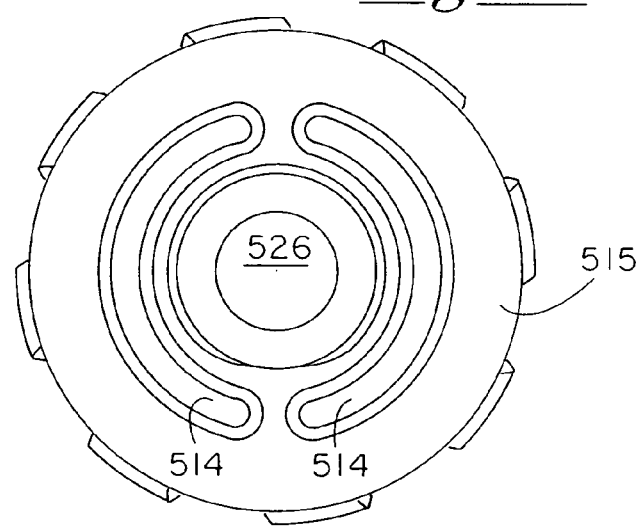
FIG. 19 is a bottom end view of the graft anchoring apparatus illustrated in FIG. 18.

The rotational actuation of sleeve member 512 described above is useful in inserting sleeve member 512 into a graft channel bored into a fixed structure, such as a bone. Preferably, sleeve member 512 is frictionally secured within such a graft channel so as to securely anchor a graft suture thereat. In some embodiments of the present invention, external surface features are disposed on outer surface 538 of sleeve member 512 so as to enhance a friction fit of sleeve member 512 within the graft channel. Such external features may further assist in the operable insertion of sleeve member 512 in the graft channel. For example, threads 540 may be disposed on outer surface 538 of sleeve member 512 in order to facilitate threadable insertion of sleeve member 512 into the graft channel. Such threadable insertion is preferably actuated by engagement of a tool such as a screwdriver within actuation aperture 532. Other features, such as ribs 542, may be disposed at outer surface 538 of sleeve member 512, as illustrated in FIGS. 18 and 19, to assist in the frictional engagement of sleeve member 512 within the graft channel. In preferred embodiments, however, a sufficient degree of frictional engagement between sleeve member 512 and the wall of the graft channel is obtained merely through the specific sizing of sleeve member 512 with respect to the diameter of the graft channel. Specifically, the outer diameter of sleeve member 512 is preferably substantially equal to the internal diameter of the graft channel, so as to effect a friction fit when sleeve member 512 is inserted therein.

Apparatus 510 preferably further includes a plug member 560 that is configured for mating engagement within axial opening 526 of sleeve member 512. Plug member 560 may be matingly engaged within axial opening 526 through a variety of techniques, such as by press fitting, or by threadably inserting plug member 560 in axial opening 526. As such, wall 527 of axial opening 526 and at least a portion of external surface 562 of plug member 560 may be correspondingly threaded to enable the threadable insertion of plug member 560 into axial opening 526.

Preferably, outer diameter $D_1$ of plug member 560 is somewhat larger than $D_2$ of axial opening 526, such that insertion of plug member 560 into axial opening 526 causes inner wall 524 of sleeve member 512 to expand outwardly toward outer wall 522 thereof. As such, the insertion of plug member 560 into axial opening 526 operably compresses suture channels 514. To assist in the operable insertion of plug member 560 into axial opening 526, plug member 560 is preferably configured as a truncated conical frustum, with first end 564 of plug member 560 having a smaller diameter than second end 566 thereof. In such a manner, progressive insertion of plug member 560 into axial opening 526 progressively displaces inner wall 524 toward outer wall 522 in order to operably compress suture channels 514.

Apparatus 510 preferably enables anchoring of the graft suture within suture channels 514 by first drawing a first end of one or more graft sutures into one or more suture channels 514, and subsequently inserting plug member 560 into axial opening 526 in order to compress suture channels 514 upon respective graft sutures disposed therein. Such compression acts to frictionally secure the graft sutures within respective suture channels 514, and thereby anchor the graft suture to the fixed structure in which apparatus 510 is frictionally engaged. One or more actuation apertures 572 may be provided at second end 566 of plug member 560 in order to assist in engaging plug member 560 within axial opening 526. Such actuation aperture 572 is preferably specifically configured for engagement with an actuation tool such as a screwdriver of the like. As such, actuation aperture 572 may be a hexagonal bore, or series of bores that correlate to a specific actuation tool useful in combination with the present invention.

An important aspect of the embodiment of the present invention illustrated in FIGS. 16-20 is the operable compression of suture channels 514 upon insertion of plug member 560 into axial opening 526 of sleeve member 512. As such, plug member 560 is preferably less resilient than the material of sleeve member 512 that is operably disposed between plug member 560 and suture channels 514. In the embodiment illustrated in FIGS. 16-19, such material is represented by inner wall 524 of sleeve member 512. For purposes of simplicity in manufacture, however, it is desired that sleeve member 512 be fabricated from a uniform material, though it is contemplated that certain portions of sleeve member 512 may be manufactured from materials different than other portions of sleeve member 512.

Accordingly, it is desired that sleeve member 512 is fabricated from a relatively resilient material. Moreover, it is desired that each of the components of apparatus 510 be fabricated from inert, bio-compatible, and durable materials. A variety of polymeric materials fit the criteria identified above as being desired in the apparatus of the present invention. Other non-polymeric materials may instead be utilized in the manufacture of the components of apparatus 510. Example materials useful in the production of the components of the present invention include polypropylene, nylon, acetal, polycarbonate, and high melt flow liquid crystal polymer. A particularly preferred material for use in the manufacture of sleeve member 512 is Ticona Zectra MT 1300. Particularly preferred materials useful in the manufacture of plug member 560 include Ticona Celcon MT24U01, which is a high melt flow grade of acetal, or a polycarbonate sold under the trade name Dow Calibre 2061 22MFR, sold by Dow Chemical of Midland, Mich. Of course, a wide variety of other materials may be utilized in the manufacture of the individual components of the present invention.

In a particularly preferred embodiment, plug member 560 is manufactured from a material that is less resilient than sleeve member 512, such that insertion of plug member 560 into axial opening 526 of sleeve member 512 compresses suture channels 514 without substantially compressing plug member 560. Such relative resiliency of the materials making up plug member 560 and sleeve member 512 assists in the effectiveness of the anchoring apparatus 510 of the present invention.

In view of the above, a preferred method for anchoring a graft segment to a fixed structure in vivo includes forming a graft channel in the fixed structure and affixing a first end of a graft suture to the graft segment. The second end of the graft suture is then passed through a respective one of suture channels 514 in sleeve member 512. Plug member 560 is then preferably inserted into axial opening 526 of sleeve member 512 to compress suture channels 514 upon the respective graft suture disposed therein thereby securing the suture in the suture channels 514.

Figure 20:
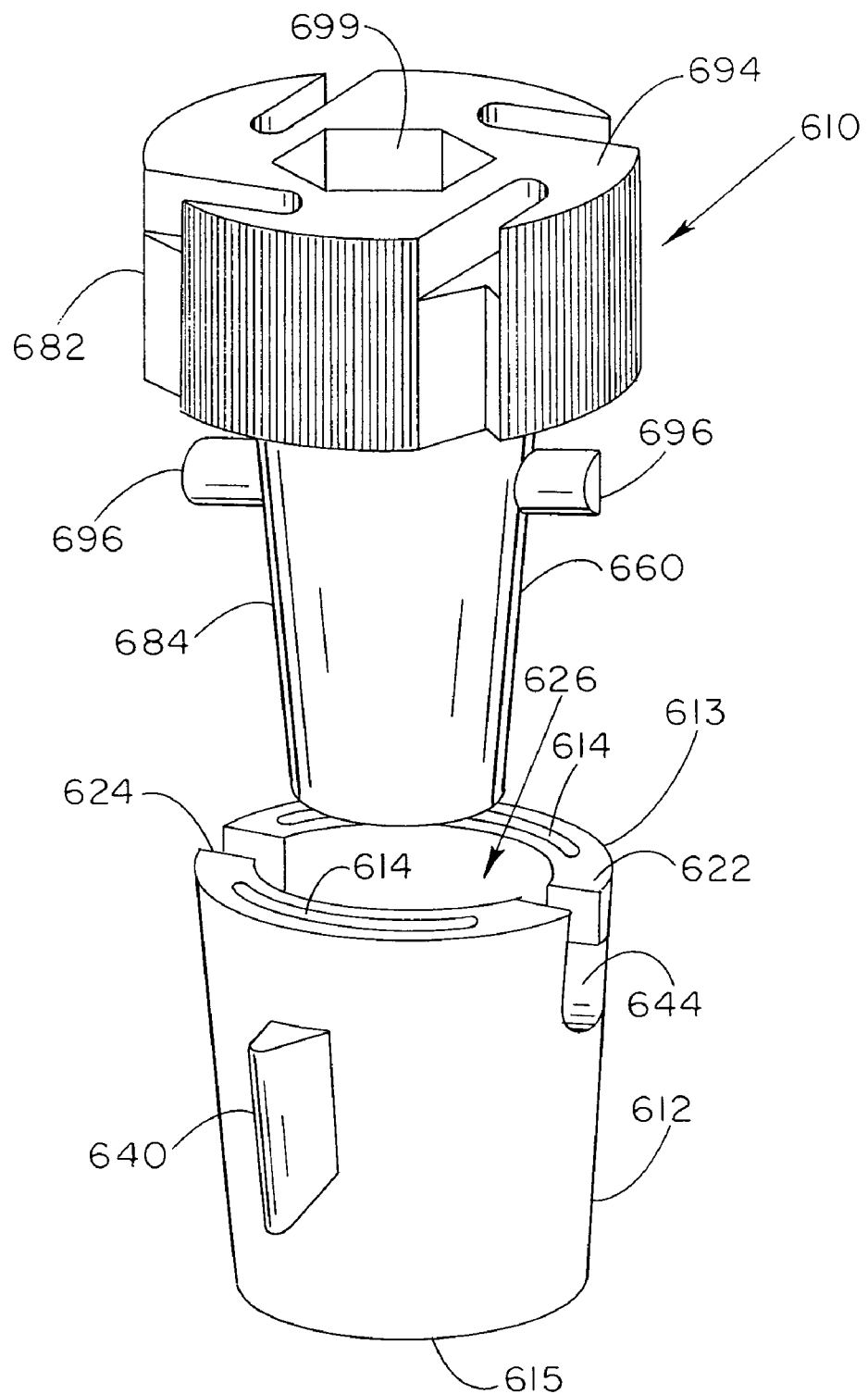
FIG. 20 is a perspective view of a graft anchoring apparatus of the present invention.

A further embodiment of the present invention is illustrated in FIG. 20, wherein graft anchoring apparatus 610 includes a sleeve member 612 that acts as a suture guide means and further having first suture channels 614 extending axially therethrough. Preferably, sleeve member 612 is constructed in similar fashion to sleeve member 512 illustrated in FIGS. 16-19, with first suture channels 614 being sized and configured to receive a graft suture therein. Graft anchoring apparatus 610 preferably further includes a plug member 660 that operably acts as described above with reference to FIGS. 16-19, by operably compressing the one or more first suture channels 614 upon insertion into axial opening 626 of sleeve member 612. As described above, such compression of first suture channels 614 occurs through expansion of inner wall 624 toward outer wall 622 as a result of the relatively "oversized" plug member 660 being inserted into axial opening 626.

Figure 20A:
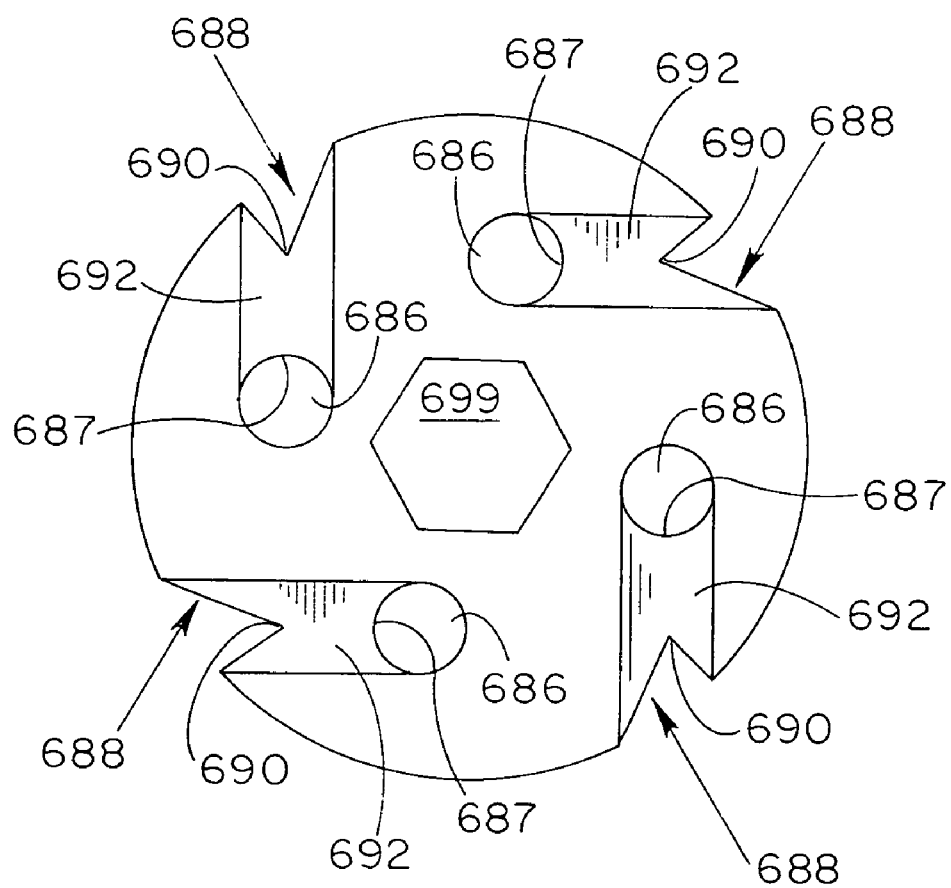
FIG. 20A is a top end view of a portion of the graft anchoring apparatus illustrated in FIG. 20.

Preferably, plug member 660 further includes a cap portion 682 that may be removably or fixedly secured to trunk portion 684 of plug member 660. As shown in FIG. 20, cap portion 682 preferably includes one or more second suture channels 686 extending axially therethrough, which second suture channel 686 are preferably in axial alignment with first suture channels 614 when plug member 660 is fully engaged with sleeve member 612. Second suture channels 686 preferably axially extend through cap portion 682, as best illustrated in FIG. 20A. As further illustrated therein, cap portion 682 of plug member 660 preferably includes locking notches 688 associated with and disposed adjacent to second suture channels 686. Such locking notches 688 preferably have a substantially v-shaped cross-section for operably grasping a first end of a graft suture at respective apexes 690 thereof through frictional resistance. Locking notches 688 are preferably oriented in spaced parallel relationship with second suture channels 686. Such a relative orientation assists in the securement of the first end of the graft suture, in that two relatively high friction points are created at lip 687 formed at the junction of the respective second graft channels 686 and respective ledges 692, and at the intersection of respective apexes 690 and such ledges 692. As such, the first end of the graft suture is passed from second end 615 through first end 613 of sleeve member 612, and into and through respective second suture channels 686 and over respective ledges 692 into locking notches 688 to frictionally secure and anchor such graft suture at graft anchoring apparatus 610. Although the embodiment illustrated in FIGS. 20 and 20A illustrate ledges 692, it is contemplated that respective second suture channels may terminate at upper surface 694 of cap portion 682, so as to eliminate the need for respective ledges 692.

Plug member 660 is preferably matingly engageable with sleeve member 612. As described above, a variety of mechanisms and configurations are contemplated by the present invention for providing a mating engagement between plug member 660 and sleeve member 612. For example, such engagement may be in the form of slidable friction fit, threadable engagement, or another type of engagement. The embodiment illustrated in FIG. 20 demonstrates a further example of a mechanism for matingly engaging plug member 660 to sleeve member 612. In this embodiment, sleeve member 612 includes substantially "L"-shaped slots extending from first end 613 thereof. Such slots are preferably specifically configured to operably receive corresponding protrusions 696 radially extending from trunk portion 684 of plug member 660. To securely engage plug member 660 into axial opening 626 of sleeve member 612, radial protrusions 696 are operably inserted into respective slots 644, and plug member 660 is then rotated to arrange radial protrusions 696 at the lock portions 645 of the respective slots 644. In such an orientation, axial displacement of plug member 660 relative to sleeve member 612 is prevented.

As shown in FIGS. 20 and 20A, cap portion 682 of plug member 660 may include friction ridges 698 on an outer surface thereof for enhancing a user's grip thereupon during engagement of plug member 660 to sleeve member 612. In addition, an actuation aperture 699 may further be provided in upper surface 694 of cap portion 682 for receiving an actuation tool such as a screwdriver or the like. Actuation aperture 699 may therefore may be a single aperture or a series of apertures oriented in a specific manner that corresponds to the configuration of a respective actuation tool for inserting plug member 660 into sleeve member 612. Additionally, sleeve member 612 may also include one or more projections 640 extending outwardly from outer surface 638 for enhancing the friction fit of sleeve member 612 within a respective graft channel formed in the respective fixed structure.

Figure 21:
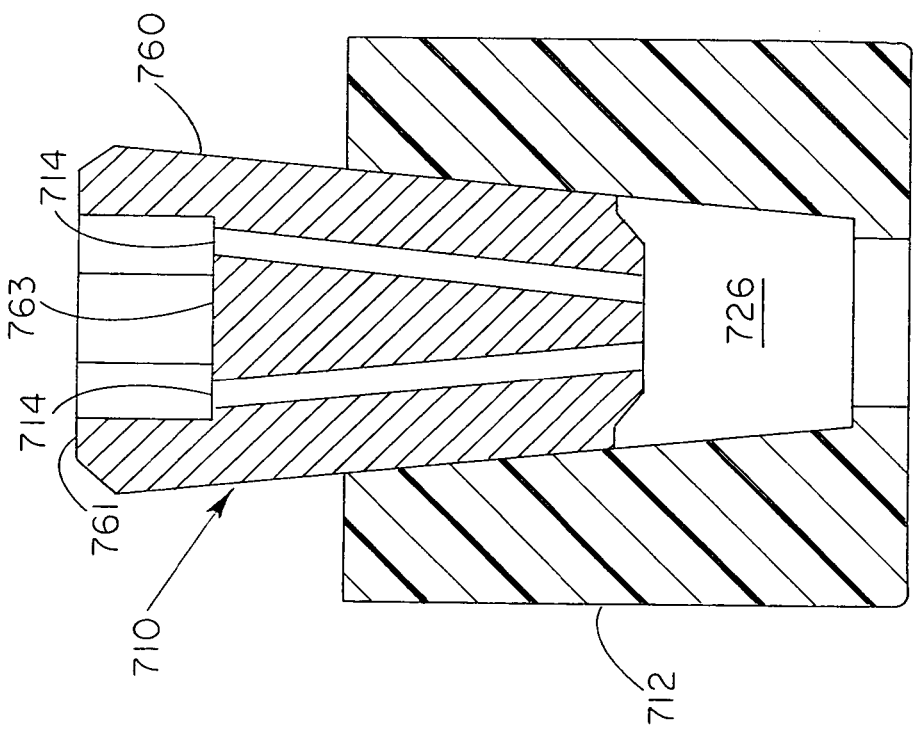
FIG. 21 is a side cross-sectional view of a graft anchoring apparatus of the present invention.

A further embodiment of the present invention is illustrated in FIG. 21, wherein graft anchoring apparatus 710 includes a plug member 760 that is matingly engageable within an axial opening 726 of sleeve member 712. The distinction of the embodiment illustrated in FIG. 21 over those shown in FIGS. 16-20 is in the fact that suture channels 714 are preferably disposed in plug member 760 instead of, or in addition to, such suture channels being disposed in sleeve member 712.

Otherwise, the conceptual utility of graft anchoring apparatus 710 is similar to that described with reference to FIGS. 16-20, in that the mating engagement of plug member 760 in axial opening 726 of sleeve member 712 operably causes suture channels to compress, and to thereby secure graft sutures disposed therewithin to graft anchoring apparatus 710. Preferably, the mating engagement of plug member 760 within axial opening 726 of sleeve member 712 is through frictional and/or threadable engagement, though other mechanisms for providing a mating engagement therebetween are also contemplated for use in the present invention. To assist in the operation of compressing suture channel 714 upon the mating engagement of plug member 760 and sleeve member 712, sleeve member 712 is preferably less resilient than plug member 760, such that insertion of plug member 760 into axial opening 726 causes outer portion 761 of plug member 760 to deflect inwardly toward inner portion 763 thereof. Such deflection operably compresses suture channels 714 to thereby frictionally engage one or more graft sutures operably disposed therein.

Figure 22:
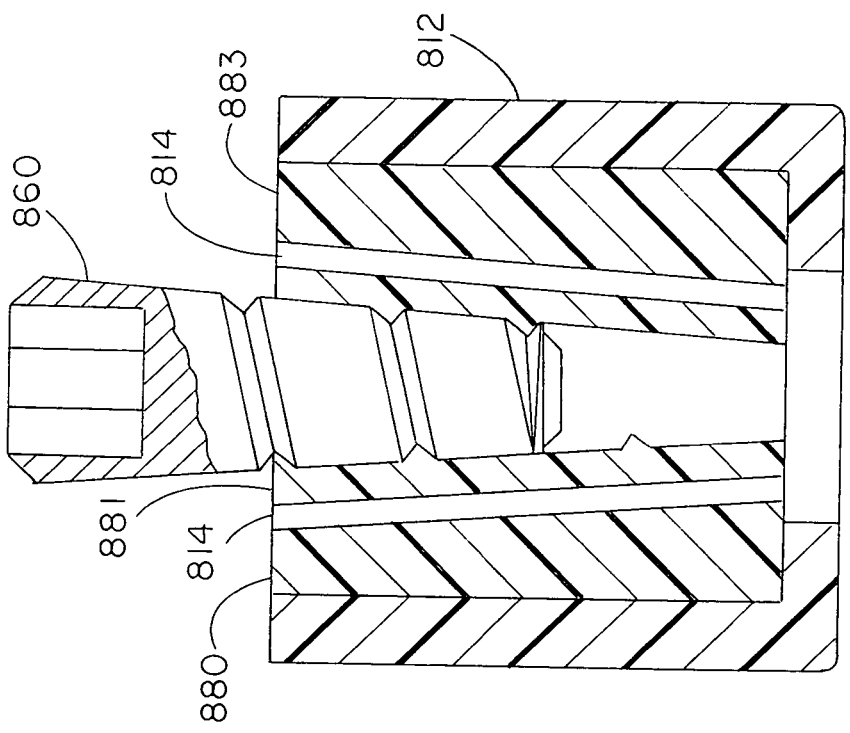
FIG. 22 is a side cross-sectional view of a graft anchoring apparatus of the present invention.

In a still further embodiment of the present invention, graft anchoring apparatus 810, as shown in FIG. 22, preferably includes a sleeve member 812, a plug member 860, and an intermediate member 880. In this embodiment, suture channels 814 are disposed in intermediate member 880, such that plug member 860 may be operably inserted into a second axial opening 827 in intermediate member 880 to thereby compress suture channels 814 upon a graft suture operably disposed therein. Intermediate member 880 is preferably operably disposed in first axial opening 826 in sleeve member 812. To assist in the operable compression of suture channels 814 during the engagement of plug member 860 into second axial opening 827, intermediate member 880 is preferably manufactured from a material that is more resilient than that of the sleeve member 812 and plug member 860. In such an arrangement, the operable insertion of plug member 860 into second axial opening 827 causes inner wall 881 to displace toward outer wall 883 of intermediate member 880, while sleeve member 812 rigidly maintains an outer circumferential boundary for intermediate member 880. Such displacement of inner wall 881 toward outer wall 883, with outer wall 883 being maintained in a fixed orientation, results in the compression of suture channels 814. As described above, such compression of suture channels 814 frictionally secures graft sutures disposed therein, so as to securely anchor such graft sutures to graft anchoring apparatus 810 disposed in a graft channel bored within a fixed structure, such as a bone.

As described above, the specific parts of graft anchoring apparatus 810 preferably matingly engage with one another through one or more of a variety of engagement mechanisms. The engagement mechanisms may include, for example, frictional engagement, threadable engagement, and other mechanisms and configurations enabling a mating engagement between respective components of graft anchoring apparatus 810.

As the embodiments illustrated in FIGS. 16-22 clearly demonstrate, a variety of configurations may be developed to achieve the underlying unique utility of the graft anchoring apparatus of the present invention. Specifically, the graft anchoring apparatus of the present invention preferably includes one or more suture channels configured to operably receive a graft suture therein or therethrough while in an unstressed state. The apparatus of the present invention is preferably configured to cause operable compression of such suture channels through the mating engagement of two or more separate components being manufactured of similar or distinct materials. Such compression is typically generated by engaging specific components that force the suture channel-containing member to yield during the insertion of, for example, a specifically-configured plug member.

It should be understood by those of ordinary skill in the art that such a functionality may be brought about through a variety of configurations involving one or more channels that may be operably compressed upon a graft suture disposed therein to thereby frictionally secure such graft suture to a fixed structure in-vivo. Accordingly, the one or more graft channels may be disposed in one or more distinct components making up the apparatus of the present invention. In addition, such graft channels may be disposed in a single monolithic component that is configured to temporarily receive a displacement member that causes the operable displacement of certain portions of such a monolithic element to cause compression of the suture channels upon graft sutures disposed therein. Accordingly, the plug members described with reference to FIGS. 16-22 hereof may act as displacement members to be permanently or temporarily inserted within a corresponding axial opening so as to cause compression of respective suture channels. In embodiments where the plug member is only temporarily inserted in a respective axial opening in the graft anchoring apparatus, the material of the component having respective graft channels disposed therein should be a malleable material rather than a resilient material, so that displacement of corresponding portions thereof to cause compression of the suture channels is a permanent modification of the shape of the component housing the suture channels.

Figure 23:
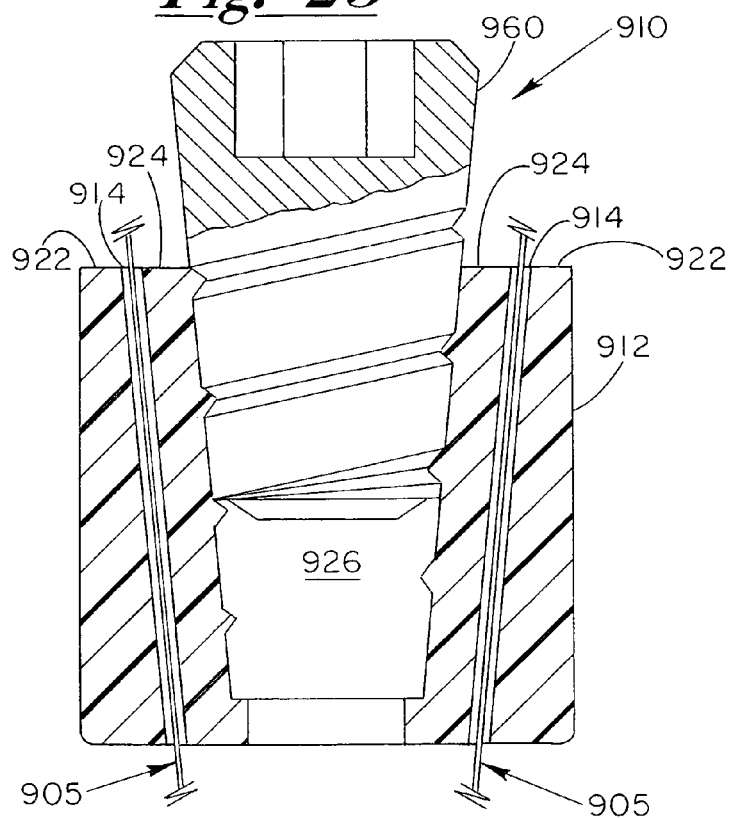
FIG. 23 is a side cross-sectional view of a graft anchoring apparatus of the present invention.
Figure 24:
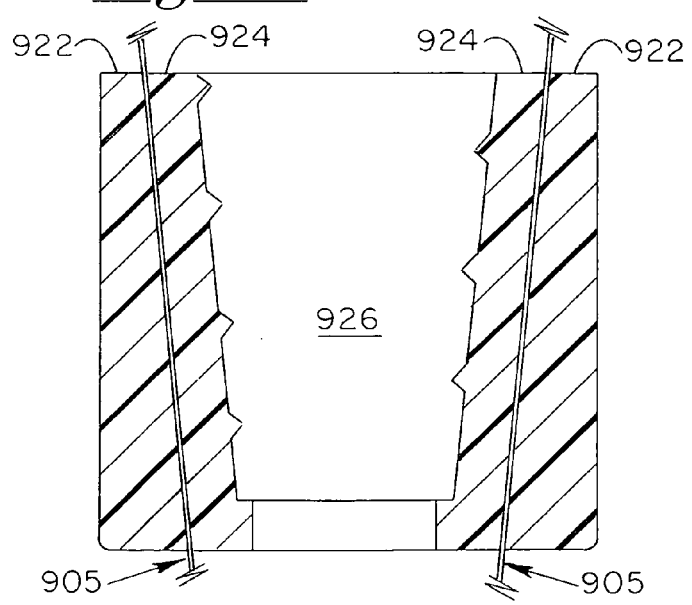
FIG. 24 is a side cross-sectional view of a portion of the graft anchoring apparatus illustrated in FIG. 23 subsequent to a displacement procedure.

An example of such an embodiment is illustrated in FIGS. 23 and 24, wherein sleeve member 912 is fabricated from a malleable material, such that insertion of plug member 960 into axial opening 926 of sleeve member 912 permanently displaces inner wall 924 toward outer wall 922 so as to permanently compress respective suture channels 914 upon graft sutures 905 disposed therein. Certain thermosetting and thermoplastic polymers provide an example malleable material for use in such an embodiment. FIG. 24 illustrates the resultant configuration of sleeve member 912 subsequent to the configurational modification incurred through the temporary insertion of plug member 960 into axial opening 926 of sleeve member 912.

Figure 25:
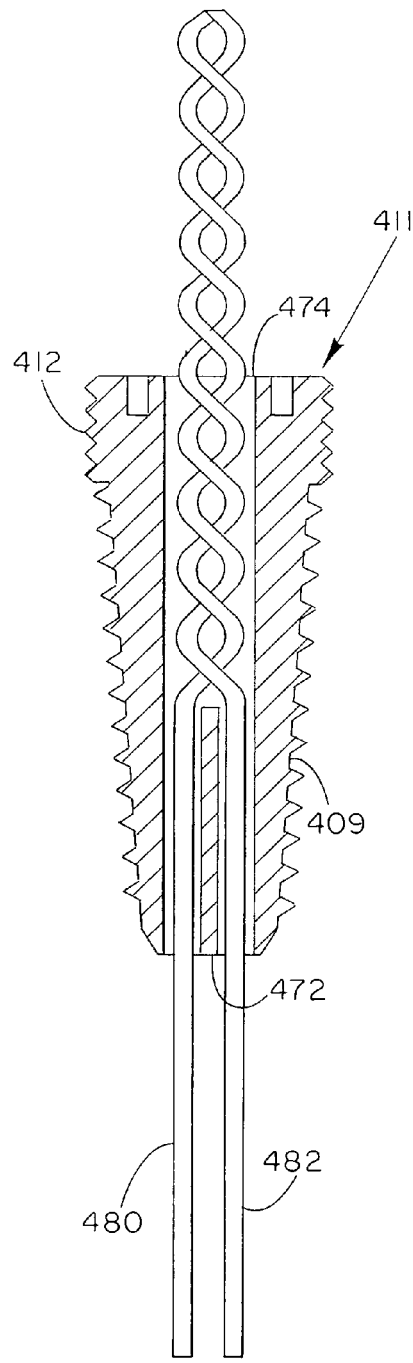
FIG. 25 is a side cross-sectional view of a graft anchoring device of the present invention.
Figure 26:
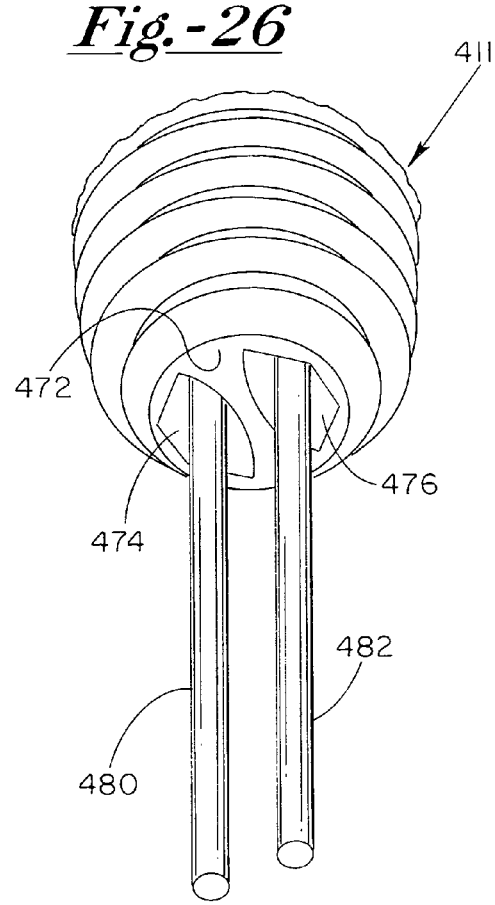
FIG. 26 is a perspective view of a portion of the graft anchoring device of the present invention illustrated in FIG. 25.

A further aspect of the present invention is illustrated in FIGS. 25 and 26, wherein a graft anchoring device akin to those illustrated in FIGS. 13-15 includes a divider portion 472 disposed in open bore 474 of fastener 411. As shown in the cross-sectional view of FIG. 25, fastener 411 includes a proximal portion 412 and a distal portion 409, with the divider portion 472 being disposed in at least the distal portion of open bore 474. In other embodiments, however, divider portion 472 may extend through an entire length of open bore 474.

A perspective view of fastener 411 is shown in FIG. 26, wherein divider portion 472 is preferably formed of a bridging material extending through open bore 474 between respective portions of interior wall 476 of fastener 411. Such a divider portion 472 divides at least a portion of open bore 474 into a plurality of distinct suture pathways through which individual sutures 480, 482 may operably pass. In such a manner, divider portion 472 prevents graft sutures 480, 482 from inter-winding about one another at distal portion 409 of fastener 411 during the threadable insertion of fastener 411 into a respective graft channel in the fixed structure.

It has been found by the Applicants that winding of two or more graft sutures about one another adjacent to the graft segment may cause the graft segment itself to twist. Such movement of the graft segment itself is typically undesired. As such, divider portion 472 isolates any winding of graft sutures 480, 482 about one another to portions thereof that are spaced from the graft segment. Such isolation prevents the graft segment from twisting during the rotating fastener installation procedure. Although divider portion 472 is illustrated in FIGS. 25 and 26 as creating two distinct suture pathways, it is contemplated by the present invention that divider portion 472 may be configured so as to form more than two of such distinct suture pathways through open bore 474 of fastener 411.

As described above, the various embodiments of the graft anchoring device of the present invention may incorporate elements which are fabricated from biocompatible materials. Alternatively, such elements making up the graft anchoring device of the present invention may be fabricated from other relatively strong materials. Examples of such materials include polymeric materials such as perfluorinated copolymers, and non-polymeric materials such as stainless steel or the like. Other polymeric and non-polymeric materials are also contemplated by the present invention as being useful in the components thereof.

The anchoring device of the present invention may be utilized in a wide variety of applications for easily and consistently securing graft segments in place. A particular example of an additional procedure in which the anchoring device may be utilized is in rotator cuff repair surgery. Additionally, such an anchoring device may be utilized in other medical and non-medical applications.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A graft anchoring apparatus for anchoring a graft segment to a fixed structure in vivo, said graft anchoring apparatus comprising:
   a suture receiving member having an inner wall and an outer wall defining one or more suture receptacles therebetween, and an axial opening extending substantially parallel to said one or more suture receptacles; and
   a fixing member that is specifically configured to matingly engage within said axial opening of said suture receiving member, such engagement resiliently radially outwardly displacing said inner wall toward said outer wall to correspondingly compress said one or more suture receptacles to a degree sufficient to secure a respective graft suture therewithin, said suture receiving member being specifically configured to be frictionally fit in a graft channel in said fixed structure.

2. A graft anchoring apparatus as in claim 1 wherein said fixing member threadably engages with said suture receiving member.

3. A graft anchoring apparatus as in claim 1 wherein said one or more suture receptacles comprise one or more channels extending axially through said suture receiving member.

4. A graft anchoring apparatus as in claim 1 wherein said fixing member threadably engages within said axial opening.

5. A graft anchoring apparatus as in claim 1 wherein said suture receiving member threadably engages within said graft channel.

6. An apparatus for anchoring a graft segment to a fixed structure in vivo, comprising:
   a sleeve member having an inner wall and an outer wall defining one or more suture channels extending axially therebetween, and an axial opening extending adjacent to said one or more suture channels from a first end of said sleeve member; and
   a plug member being configured for mating engagement within said axial opening of said sleeve member, such engagement radially outwardly displacing said inner wall of said sleeve member and correspondingly compressing said one or more suture channels to frictionally secure a respective graft suture therein.

7. An apparatus as in claim 6 wherein said plug member threadably engages within said axial opening.

8. An apparatus as in claim 6 wherein said axial opening is inwardly tapered from said first end of said sleeve member.

9. An apparatus as in claim 8 wherein said plug member is configured as a truncated conical frustum.

10. An apparatus as in claim 6 wherein said sleeve member is specifically configured for frictional engagement within a graft channel in said fixed structure.

11. An apparatus as in claim 10 wherein said sleeve member includes threads disposed on an outer surface thereof for threadably engaging within said graft channel.

12. An apparatus as in claim 6 wherein said sleeve member includes a stop flange adjacent to a second end of said sleeve member substantially opposite said first end, said stop flange extends radially inwardly into said axial opening.

13. An apparatus as in claim 6 wherein said one or more suture channels are perimetorally disposed about said axial opening.

14. An apparatus as in claim 6, including one or more actuation apertures in said plug member.

15. An apparatus as in claim 6, including one or more actuation apertures in said sleeve member.

* * * * *